(12) United States Patent
Benayahu

(10) Patent No.: US 7,829,296 B2
(45) Date of Patent: Nov. 9, 2010

(54) KINESIN POLYPEPTIDES, POLYNUCLEOTIDES ENCODING SAME AND COMPOSITIONS AND METHODS OF USING SAME

(75) Inventor: Dafna Benayahu, Herzlia (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 241 days.

(21) Appl. No.: 11/919,196

(22) PCT Filed: Apr. 25, 2006

(86) PCT No.: PCT/IL2006/000506

§ 371 (c)(1),
(2), (4) Date: Oct. 24, 2007

(87) PCT Pub. No.: WO2006/114788

PCT Pub. Date: Nov. 2, 2006

(65) Prior Publication Data

US 2009/0280123 A1    Nov. 12, 2009

Related U.S. Application Data

(60) Provisional application No. 60/674,293, filed on Apr. 25, 2005.

(51) Int. Cl.
*G01N 33/53* (2006.01)
(52) U.S. Cl. ......................................... 435/7.1; 436/518
(58) Field of Classification Search ........................ None
See application file for complete search history.

(56) References Cited

FOREIGN PATENT DOCUMENTS

| WO | WO 02/12268 | 2/2002 |
|----|-------------|--------|
| WO | WO 2004067779 | * 8/2004 |

OTHER PUBLICATIONS

Wells (1990) Biochemistry 29: 8509-8517.*
Ngo et al. (1995) "The Protein Folding Problem and Tertiary Structure Prediction, Chapter 14: Computational Complexity Protein Structure Prediction, and the Levinthal Paradox" pp. 433-506 Editor by Merz et al.*
Bork (2000) Genome Research 10:398-400; Skolnick (2000) Trends in Biotech. 18: 34-39.*
Smith et al. (1997) Nature Biotechnology 1999 15: 1222-1223).*
Luboshits et al. "A Unique Human Kinesin-Related Protein Expressed by Marrow Stromal Cells", Journal of Bone and Mineral Research, 15, (Suppl. 1): S383, 2000. & 22nd Annual Meeting of the American Society for Bone and Mineral Research, Toronto, CA, Sep. 2002.
Luboshits et al. "MS-KIF18A, New Kinesin; Structure and Cellular Expression", Gene: An International Journal on Genes and Genomes, 351: 19-28, 2005.
Wang et al. "Method for Preparing Male-Sterile Mouse Model", Database Caplus Chemical Abstracts Service, CN1795929, 2004. Abstract.
International Preliminary Report on Patentability Dated Nov. 8, 2007 From the International Bureau of WIPO Re.: Application No. PCT/IL2006/000506.

* cited by examiner

*Primary Examiner*—Jacob Cheu

(57) ABSTRACT

An isolated polynucleotide comprising a nucleic acid sequence encoding a KIF18A polypeptide being expressed in mesenchymal stem cells is disclosed. Methods of detecting same are disclosed as well as methods of using same for modulating estrogen signaling in cells.

4 Claims, 16 Drawing Sheets

B. MS-KIF18A

Erythroid EST
BG944537

Leomyosarcoma
BC035917

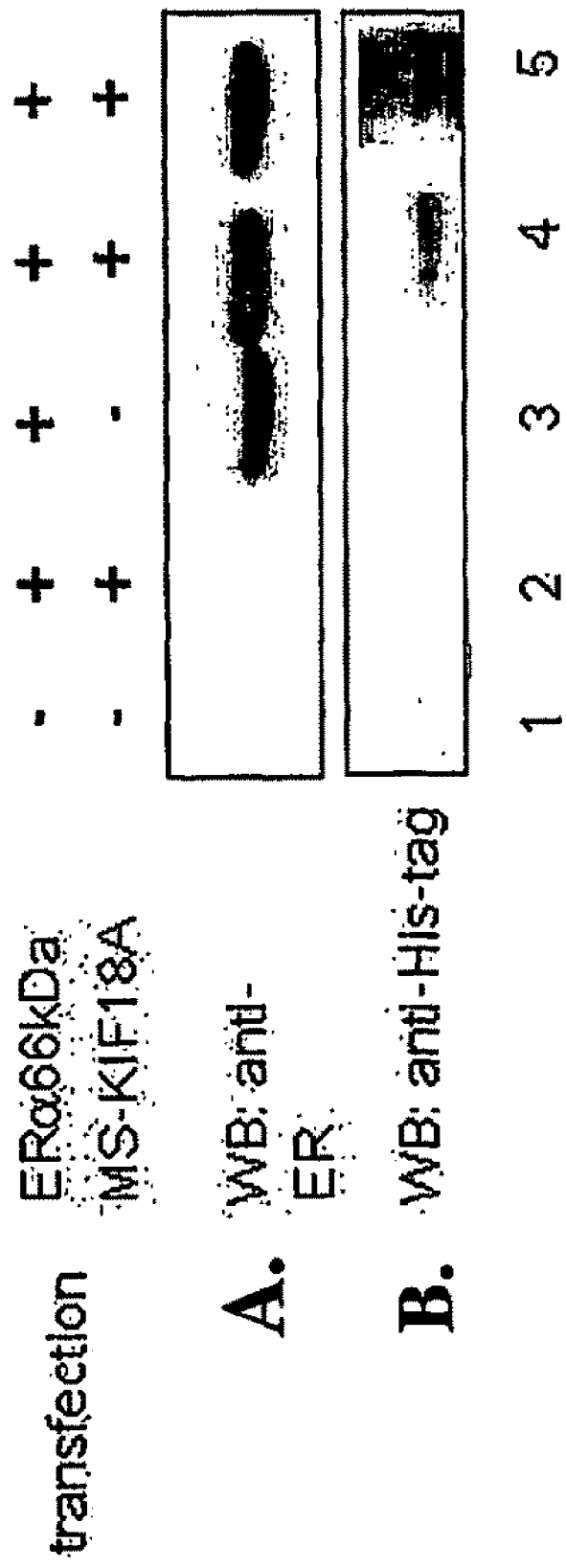
FIGs. 14A-B

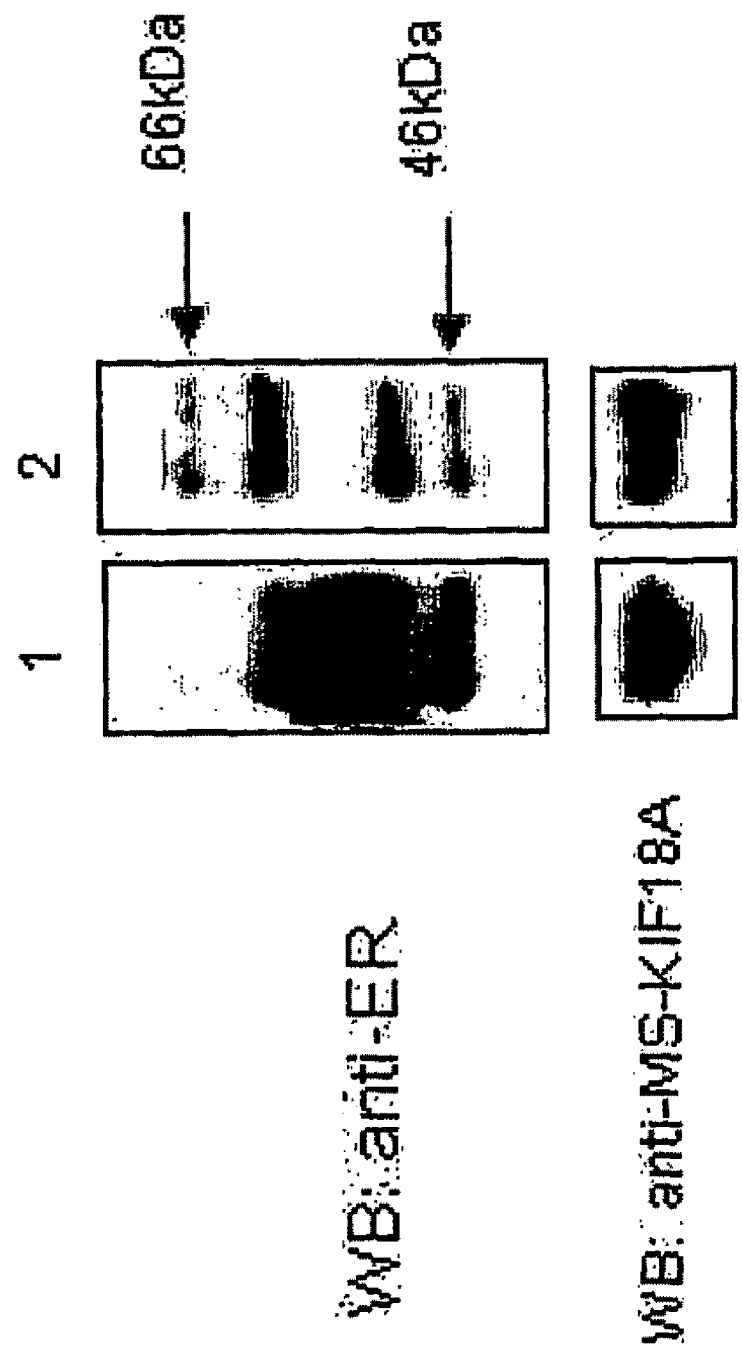

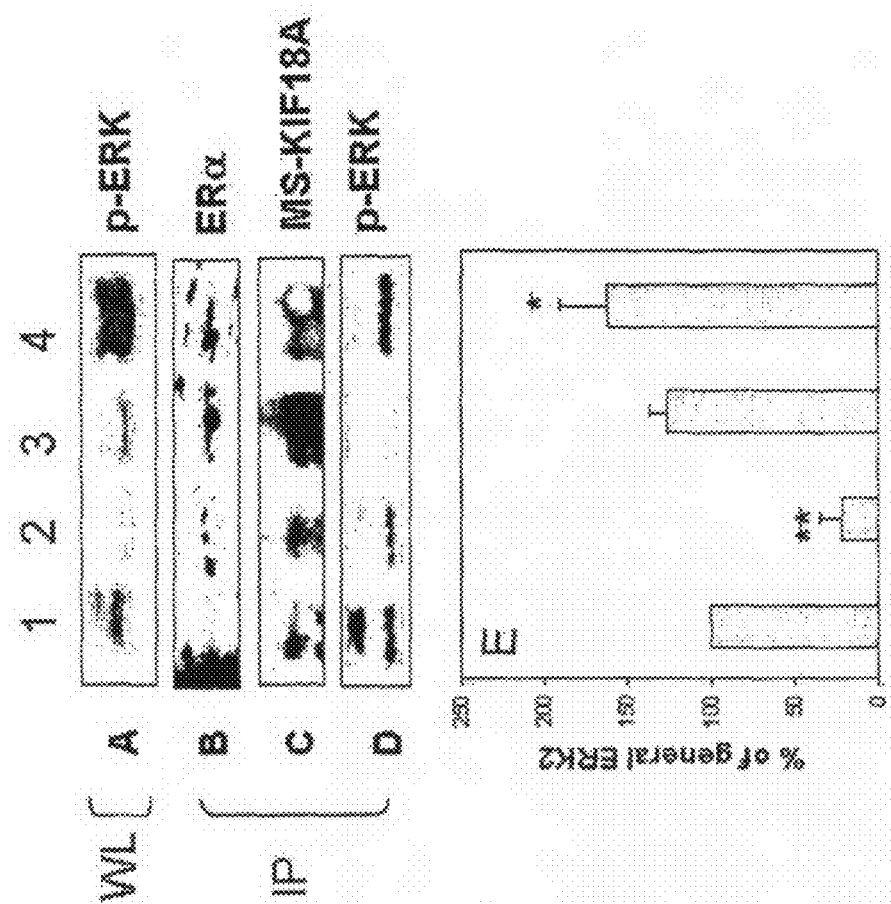
FIGs. 16A-E

SEQUENCE LISTING

<160> NUMBER OF SEQ ID NOS: 12

<210> SEQ ID NO 1
<211> LENGTH: 3407
<212> TYPE: DNA
<213> ORGANISM: Homo sapiens

<400> SEQUENCE: 1

```
ggacattaaa gtgaagtggt tgcggtaacc tggcctgggc ctgaagtgag tgagaggcac      60
atgaagagaa gtattcaagt atttatacag ataggaatca agataatcaa caatgtctgt     120
cactgaggaa gacctgtgcc accatatgaa agtagtagtt cgtgtacgtc cggaaaacac     180
taaagaaaaa gcagctggat ttcataaagt ggttcatgtt gtggataaac atatcctagt     240
ttttgatccc aaacaagaag aagtcagttt tttccatgga aagaaaacta caaatcaaaa     300
tgttataaag aaacaaaata aggatcttaa atttgtattt gatgctgttt ttgatgaaac     360
gtcaactcag tcagaagttt ttgaacacac tactaagcca attcttcgta gttttttgaa     420
tggatataat tgcacagtac ttgcctatgg tgccactggt gctgggaaga cccacactat     480
gctaggatca gctgatgaac ctggagtgat gtatctaaca atgttacacc tttacaaatg     540
catggatgag attaaagaag agaaaatatg tagtactgca gtttcatatc tggaggtata     600
taatgaacag attcgtgatc tcttagtaaa ttcagggcca cttgctgtcc gggaagatac     660
ccaaaaaggg gtggtcgttc atggacttac tttacaccag cccaaatcct cagaagaaat     720
tttacattta ttggataatg aaacaaaaa caggacacaa catcccactg atatgaatgc     780
cacatcttct cgttctcatg ctgttttcca aatttacttg cgacaacaag acaaaacagc     840
aagtatcaat caaaatgtcc gtattgccaa gatgtcactc attgacctgg caggatctga     900
gcgagcaagt acttccggtg ctaaggggac ccgatttgta gaaggcacaa atattaatag     960
atcactttta gctcttggga atgtcatcaa tgccttagca gattcaaaga gaaagaatca    1020
gcatatccct tacagaaata gtaagcttac tcgcttgtta aaggattctc ttggaggaaa    1080
ctgtcaaact ataatgatag ctgctgttag tccttcctct gtattctacg atgcacata    1140
taacactctt aagtatgcta accgggcaaa ggacattaaa tcttctttga agagcaatgt    1200
tcttaatgtc aataatcata taactcaata tgtaaagatc tgtaatgagc agaaggcaga    1260
gatttttattg ttaaaagaaa actaaaagc ctatgaagaa cagaaagcct tcactaatga    1320
aaatgaccaa gcaaagttaa tgatttcaaa ccctcaggaa aaagaaatcg aaaggtttca    1380
agaaatcctg aactgcttgt tccagaatcg agaagaaatt agacaagaat atctgaagtt    1440
ggaaatgtta cttaaagaaa atgaacttaa atcattctac caacaacagt gccataaaca    1500
aatagaaatg atgtgttctg aagacaaagt agaaaaggcc actggaaaac gagatcatag    1560
acttgcaatg ttgaaaactc gtcgctccta cctggagaaa aggagggagg aggaattgaa    1620
gcaatttgat gagaatacta attggctcca tcgtgtcgaa aaagaaatgg gactcttaag    1680
tcaaaacggt catattccaa aggaactcaa gaaagatctt cattgtcacc atttgcacct    1740
ccagaacaaa gatttgaaag cacaaattag acatatgatg gatctagctt gtcttcagga    1800
acagcaacac aggcagactg aagcagtatt gaatgcttta cttccaaccc taagaaaaca    1860
atattgcaca ttaaaagaag ccggcctgtc aaatgctgct tttgaatctg acttcaaaga    1920
gatcgaacat ttggtagaga ggaaaaagt ggtagtttgg gctgaccaaa ctgccgaaca    1980
accaaagcaa aacgatctac cagggatttc tgttcttatg acctttccac aacttggacc    2040
agttcagcct attccttgtt gctcatcttc aggtggaact aatctggtta agattcctac    2100
agaaaaaaga actcggagaa aactaatgcc atctcccttg aaaggacagc atactctaaa    2160
gtctccacca tctcaaagtg tgcagctcaa tgattctctt agcaaagaac ttcagcctat    2220
tgtatataca ccagaagact gtagaaaagc ttttcaaaat ccgtctacag taaccttaat    2280
gaaaccatca tcatttacta caagttttca ggctgtcagc tcaaacataa acagtgataa    2340
```

-continued

```
ttgtctgaaa atgttgtgtg aagtagctat ccctcataat agaagaaaag aatgtggaca      2400
ggaggacttg gactctacat ttactatatg tgaagacatc aagagctcga agtgtaaatt      2460
acccgaacaa gaatcactac caaatgataa caaagacatt ttacaacggc ttgatccttc      2520
ttcattctca actaagcatt ctatgcctgt accaagcatg gtgccatcct acatggcaat      2580
gactactgct gccaaaagga aacggaaatt aacaagttct acatcaaaca gttcgttaac      2640
tgcagacgta aattctggat tgccaaacg tgttcgacaa gataattcaa gtgagaagca      2700
cttacaagaa aacaaaccaa caatggaaca taaaagaaac atctgtaaaa taaatccaag      2760
catggttaga aaatttggaa gaaatatttc aaaaggaaat ctaagataaa tcacttcaaa      2820
accaagcaaa atgaagttga tcaaatctgc ttttcaaagt ttatcaatac cctttcaaaa      2880
atatatttaa aatctttgaa agaagaccca tcttaaagct aagtttaccc aagtactttc      2940
agcaagcaga aaaatgaaac tctttgtttt cttcttttgt gttctaaaaa aataaaattt      3000
caaaagaaaa ggttgtcttt taagtttttt aaatatttgt tgccttttaa aatccctgag      3060
tgtaagttac catggtggca gcttagtttt actatgccac aacaagttga ctaggacatt      3120
ttagtaaatg gtagtgagtt aaattatctt tattattttt taaaaataag aatttagaag      3180
tggtaaaatt atgggcccaag atgtatttgg ttctctatta tgttttgata cattatttta      3240
atcatatata tgactttcct tttcaaaaat acttaagta caagtgtaaa tatatgtgcc       3300
cataaaatca ttgtaaatat tatttagtca tcacaaataa aatattgtcc cttgctactt      3360
gatatattaa agatgtagat tttaaagtga aaaaaaaaaa tttaaaa                    3407
```

<210> SEQ ID NO 2
<211> LENGTH: 898
<212> TYPE: PRT
<213> ORGANISM: Homo sapiens

<400> SEQUENCE: 2

```
Met Ser Val Thr Glu Glu Asp Leu Cys His His Met Lys Val Val
1               5                   10                  15

Arg Val Arg Pro Glu Asn Thr Lys Glu Lys Ala Ala Gly Phe His Lys
                20                  25                  30

Val Val His Val Asp Lys His Ile Leu Val Phe Asp Pro Lys Gln
            35                  40                  45

Glu Glu Val Ser Phe Phe His Gly Lys Lys Thr Thr Asn Gln Asn Val
        50                  55                  60

Ile Lys Lys Gln Asn Lys Asp Leu Lys Phe Val Phe Asp Ala Val Phe
65                  70                  75                  80

Asp Glu Thr Ser Thr Gln Ser Glu Val Phe Glu His Thr Thr Lys Pro
                85                  90                  95

Ile Leu Arg Ser Phe Leu Asn Gly Tyr Asn Cys Thr Val Leu Ala Tyr
                100                 105                 110

Gly Ala Thr Gly Ala Gly Lys Thr His Thr Met Leu Gly Ser Ala Asp
            115                 120                 125

Glu Pro Gly Val Met Tyr Leu Thr Met Leu His Leu Tyr Lys Cys Met
        130                 135                 140

Asp Glu Ile Lys Glu Glu Lys Ile Cys Ser Thr Ala Val Ser Tyr Leu
145                 150                 155                 160

Glu Val Tyr Asn Glu Gln Ile Arg Asp Leu Leu Val Asn Ser Gly Pro
                165                 170                 175

Leu Ala Val Arg Glu Asp Thr Gln Lys Gly Val Val Val His Gly Leu
```

-continued

```
                180                 185                 190
Thr Leu His Gln Pro Lys Ser Ser Glu Glu Ile Leu His Leu Leu Asp
            195                 200                 205
Asn Gly Asn Lys Asn Arg Thr Gln His Pro Thr Asp Met Asn Ala Thr
        210                 215                 220
Ser Ser Arg Ser His Ala Val Phe Gln Ile Tyr Leu Arg Gln Gln Asp
225                 230                 235                 240
Lys Thr Ala Ser Ile Asn Gln Asn Val Arg Ile Ala Lys Met Ser Leu
                245                 250                 255
Ile Asp Leu Ala Gly Ser Glu Arg Ala Ser Thr Ser Gly Ala Lys Gly
            260                 265                 270
Thr Arg Phe Val Glu Gly Thr Asn Ile Asn Arg Ser Leu Leu Ala Leu
        275                 280                 285
Gly Asn Val Ile Asn Ala Leu Ala Asp Ser Lys Arg Lys Asn Gln His
        290                 295                 300
Ile Pro Tyr Arg Asn Ser Lys Leu Thr Arg Leu Leu Lys Asp Ser Leu
305                 310                 315                 320
Gly Gly Asn Cys Gln Thr Ile Met Ile Ala Ala Val Ser Pro Ser Ser
                325                 330                 335
Val Phe Tyr Asp Asp Thr Tyr Asn Thr Leu Lys Tyr Ala Asn Arg Ala
            340                 345                 350
Lys Asp Ile Lys Ser Ser Leu Lys Ser Asn Val Leu Asn Val Asn Asn
        355                 360                 365
His Ile Thr Gln Tyr Val Lys Ile Cys Asn Glu Gln Lys Ala Glu Ile
        370                 375                 380
Leu Leu Leu Lys Glu Lys Leu Lys Ala Tyr Glu Glu Gln Lys Ala Phe
385                 390                 395                 400
Thr Asn Glu Asn Asp Gln Ala Lys Leu Met Ile Ser Asn Pro Gln Glu
                405                 410                 415
Lys Glu Ile Glu Arg Phe Gln Glu Ile Leu Asn Cys Leu Phe Gln Asn
            420                 425                 430
Arg Glu Glu Ile Arg Gln Glu Tyr Leu Lys Leu Glu Met Leu Leu Lys
        435                 440                 445
Glu Asn Glu Leu Lys Ser Phe Tyr Gln Gln Gln Cys His Lys Gln Ile
        450                 455                 460
Glu Met Met Cys Ser Glu Asp Lys Val Glu Lys Ala Thr Gly Lys Arg
465                 470                 475                 480
Asp His Arg Leu Ala Met Leu Lys Thr Arg Arg Ser Tyr Leu Glu Lys
                485                 490                 495
Arg Arg Glu Glu Glu Leu Lys Gln Phe Asp Glu Asn Thr Asn Trp Leu
            500                 505                 510
His Arg Val Glu Lys Glu Met Gly Leu Leu Ser Gln Asn Gly His Ile
        515                 520                 525
Pro Lys Glu Leu Lys Lys Asp Leu His Cys His His Leu His Leu Gln
        530                 535                 540
Asn Lys Asp Leu Lys Ala Gln Ile Arg His Met Met Asp Leu Ala Cys
545                 550                 555                 560
Leu Gln Glu Gln Gln His Arg Gln Thr Glu Ala Val Leu Asn Ala Leu
                565                 570                 575
Leu Pro Thr Leu Arg Lys Gln Tyr Cys Thr Leu Lys Glu Ala Gly Leu
            580                 585                 590
Ser Asn Ala Ala Phe Glu Ser Asp Phe Lys Glu Ile Glu His Leu Val
        595                 600                 605
```

| | | | | | | | | | | | |
|---|---|---|---|---|---|---|---|---|---|---|---|
| Glu | Arg | Lys | Lys | Val | Val | Trp | Ala | Asp | Gln | Thr | Ala | Glu | Gln | Pro |
| | 610 | | | | 615 | | | | 620 | | |

Lys Gln Asn Asp Leu Pro Gly Ile Ser Val Leu Met Thr Phe Pro Gln
625                 630                 635                 640

Leu Gly Pro Val Gln Pro Ile Pro Cys Cys Ser Ser Gly Gly Thr
                645                 650                 655

Asn Leu Val Lys Ile Pro Thr Glu Lys Arg Thr Arg Arg Lys Leu Met
                660                 665                 670

Pro Ser Pro Leu Lys Gly Gln His Thr Leu Lys Ser Pro Ser Gln
            675                 680                 685

Ser Val Gln Leu Asn Asp Ser Leu Ser Lys Glu Leu Gln Pro Ile Val
            690                 695                 700

Tyr Thr Pro Glu Asp Cys Arg Lys Ala Phe Gln Asn Pro Ser Thr Val
705                 710                 715                 720

Thr Leu Met Lys Pro Ser Ser Phe Thr Thr Ser Phe Gln Ala Val Ser
                725                 730                 735

Ser Asn Ile Asn Ser Asp Asn Cys Leu Lys Met Leu Cys Glu Val Ala
                740                 745                 750

Ile Pro His Asn Arg Arg Lys Glu Cys Gly Gln Glu Asp Leu Asp Ser
            755                 760                 765

Thr Phe Thr Ile Cys Glu Asp Ile Lys Ser Ser Lys Cys Lys Leu Pro
770                 775                 780

Glu Gln Glu Ser Leu Pro Asn Asp Asn Lys Asp Ile Leu Gln Arg Leu
785                 790                 795                 800

Asp Pro Ser Ser Phe Ser Thr Lys His Ser Met Pro Val Pro Ser Met
                805                 810                 815

Val Pro Ser Tyr Met Ala Met Thr Thr Ala Ala Lys Arg Lys Arg Lys
            820                 825                 830

Leu Thr Ser Ser Thr Ser Asn Ser Ser Leu Thr Ala Asp Val Asn Ser
            835                 840                 845

Gly Phe Ala Lys Arg Val Arg Gln Asp Asn Ser Ser Glu Lys His Leu
850                 855                 860

Gln Glu Asn Lys Pro Thr Met Glu His Lys Arg Asn Ile Cys Lys Ile
865                 870                 875                 880

Asn Pro Ser Met Val Arg Lys Phe Gly Arg Asn Ile Ser Lys Gly Asn
                885                 890                 895

Leu Arg

<210> SEQ ID NO 3
<211> LENGTH: 3451
<212> TYPE: DNA
<213> ORGANISM: Homo sapiens

<400> SEQUENCE: 3

```
gcttgggttt gaatattgtg gttgagtctg aagcgctggg aggcggacat taaagtgaag    60
tggttgcggt aacctggcct gggcctgaag tgagtgagag gcacatgaag agaagtattc   120
aagtatttat acagatagga atcaagataa tcaacaatgt ctgtcactga ggaagacctg   180
tgccaccata tgaaagtagt agttcgtgta cgtccggaaa acactaaaga aaaagcagct   240
ggatttcata aagtggttca tgttgtggat aaacatatcc tagttttga tcccaaacaa    300
gaagaagtca gttttttcca tggaaagaaa actacaaatc aaaatgttat aagaaaacaa   360
aataaggatc ttaaatttgt atttgatgct gttttgatg aaacgtcaac tcagtcagaa   420
```

```
gtttttgaac acactactaa gccaattctt cgtagttttt tgaatggata taattgcaca    480
gtacttgcct atggtgccac tggtgctggg aagacccaca ctatgctagg atcagctgat    540
gaacctggag tgatgtatct aacaatgtta ccctttaca aatgcatgga tgagattaaa    600
gaagagaaaa tatgtagtac tgcagtttca tatctggagg tatataatga acagattcgt    660
gatctcttag taaattcagg gccacttgct gtccgggaag atacccaaaa aggggtggtc    720
gttcatggac ttactttaca ccagcccaaa tcctcagaag aaattttaca tttattggat    780
aatggaaaca aaaacaggac acaacatccc actgatatga atgccacatc ttctcgttct    840
catgctgttt tccaaattta cttgcgacaa caagacaaaa cagcaagtat caatcaaaat    900
gtccgtattg ccaagatgtc actcattgac ctggcaggat ctgagcgagc aagtacttcc    960
ggtgctaagg ggacccgatt tgtagaaggc acaaatatta atagatcact tttagctctt   1020
gggaatgtca tcaatgcctt agcagattca aagagaaaga atcagcatat cccttacaga   1080
aatagtaagc ttactcgctt gttaaaggat tctcttggag gaaactgtca aactataatg   1140
atagctgctg ttagtccttc ctctgtattc tacgatgaca catataacac tcttaagtat   1200
gctaaccggg caaaggacat taaatcttct ttgaagagca atgttcttaa tgtcaataat   1260
catataactc aatatgtaaa gatctgtaat gagcagaagg cagagatttt attgttaaaa   1320
gaaaaactaa aagcctatga agaacagaaa gccttcacta atgaaaatga ccaagcaaag   1380
ttaatgattt caaaccctca ggaaaaagaa atcgaaaggt ttcaagaaat cctgaactgc   1440
ttgttccaga atcgagaaga aattagacaa gaatatctga agttggaaat gttacttaaa   1500
gaaaatgaac ttaaatcatt ctaccaacaa cagtgccata aacaaataga aatgatgtgt   1560
tctgaagaca aagtagaaaa ggccactgga aaacgagatc atagacttgc aatgttgaaa   1620
actcgtcgct cctacctgga gaaaaggagg gaggaggaat tgaagcaatt tgatgagaat   1680
actaattggc tccatcgtgt cgaaaaagaa atgggactct taagtcaaaa cggtcatatt   1740
ccaaaggaac tcaagaaaga tcttcattgt caccatttgc acctccagaa caaagatttg   1800
aaagcacaaa ttagacatat gatggatcta gcttgtcttc aggaacagca acacaggcag   1860
actgaagcag tattgaatgc tttacttcca accctaagaa aacaatattg cacattaaaa   1920
gaagccggcc tgtcaaatgc tgcttttgaa tctgacttca aagagatcga acatttggta   1980
gagaggaaaa agtggtagt ttgggctgac caaactgccg aacaaccaaa gcaaaacgat   2040
ctaccaggga tttctgttct tatgaccttt ccacaacttg gaccagttca gcctattcct   2100
tgttgctcat cttcaggtgg aactaatctg gttaagattc tacagaaaaa agaactcgg   2160
agaaaactaa tgccatctcc cttgaaagga cagcatactc taaagtctcc accatctcaa   2220
agtgtgcagc tcaatgattc tcttagcaaa gaacttcagc ctattgtata tacaccagaa   2280
gactgtagaa aagcttttca aaatccgtct acagtaacct taatgaaacc atcatcattt   2340
actacaagtt ttcaggctgt cagctcaaac ataaacagtg ataattgtct gaaaatgttg   2400
tgtgaagtag ctatccctca taatagaaga aaagaatgtg gacaggagga cttggactct   2460
acatttacta tatgtgaaga catcaagagc tcgaagtgta aattacccga caagaatca   2520
ctaccaaatg ataacaaaga cattttacaa cggcttgatc cttcttcatt ctcaactaag   2580
cattctatgc ctgtaccaag catggtgcca tcctacatgg caatgactac tgctgccaaa   2640
aggaaacgga attaacaag ttctacatca aacagttcgt taactgcaga cgtaaattct   2700
ggatttgcca acgtgttcg acaagataat tcaagtgaga agcacttaca agaaaacaaa   2760
ccaacaatgg aacataaaag aaacatctgt aaaataaatc caagcatggt tagaaaattt   2820
```

```
ggaagaaata tttcaaaagg aaatctaaga taaatcactt caaaaccaag caaaatgaag    2880
ttgatcaaat ctgcttttca agtttatca atacccttc aaaatatat ttaaaatctt      2940 tgaaagaaga cccatcttaa agctaagttt acccaagtac tttcagcaag cagaaaaatg   3000
aaactctttg ttttcttctt ttgtgttcta aaaaataaa atttcaaaag aaaaggttgt    3060
cttttaagtt tttaaatat ttgttgcctt ttaaaatccc tgagtgtaag ttaccatggt   3120
ggcagcttag ttttactatg ccacaacaag ttgactagga catttagta aatggtagtg    3180 agttaaatta tctttattat tttttaaaaa taagaattta gaagtggtaa aattatggcc   3240
caagatgtat ttggttctct attatgtttt gatacattat tttaatcata tatatgactt   3300 tcctttcaa aaatacttta agtacaagtg taaatatatg tgcccataaa atcattgtaa    3360
atattattta gtcatcacaa ataaaatatt gtcccttgct acttgatata ttaaagatgt   3420
agattttaaa gtgaaaaaaa aaaatttaaa a                                    3451
```

```
<210> SEQ ID NO 4
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 4
cgggatcctc aacaatgtct gtcactgag                                       29

<210> SEQ ID NO 5
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 5
ccgctcgagg atcaacttca ttttgcttgg                                      30

<210> SEQ ID NO 6
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 6
tgtaaagatc tgtaatgagc agaag                                           25

<210> SEQ ID NO 7
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 7
ccaagtcctc ctgtccacat                                                 20

<210> SEQ ID NO 8
<211> LENGTH: 20
<212> TYPE: DNA
<213> ORGANISM: Artificial sequence
<220> FEATURE:
<223> OTHER INFORMATION: Single strand DNA oligonucleotide
```

<400> SEQUENCE: 8
gcttgggttt gaatattgtg                                              20

<210> SEQ ID NO 9
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 9
ttgcaagtct atgatctcgt tt                                           22

<210> SEQ ID NO 10
<211> LENGTH: 14
<212> TYPE: PRT
<213> ORGANISM: Artificial sequence
<220> FEATURE:
<223> OTHER INFORMATION: Synthetic peptide

<400> SEQUENCE: 10

Thr Asn Gln Asn Val Ile Lys Lys Gln Asn Lys Asp Leu Lys
1               5                   10

<210> SEQ ID NO 11
<211> LENGTH: 3379
<212> TYPE: DNA
<213> ORGANISM: Homo sapiens

<400> SEQUENCE: 11
ctggcctggg cctgaagtga gtgagaggca catgaagaga agtattcaag tatttataca      60
gataggaatc aagataatca acaatgtctg tcactgagga agacctgtgc caccatatga    120
aagtagtagt tcgtgtacgt ccggaaaaca ctaaagaaaa agcagctgga tttcataaag    180
tggttcatgt tgtggataaa catatcctag tttttgatcc caaacaagaa gaagtcagtt    240
ttttccatgg aaagaaaact acaaatcaaa atgttataaa gaaacaaaat aaggatctta    300
aatttgtatt tgatgctgtt tttgatgaaa cgtcaactca gtcagaagtt tttgaacaca    360
ctactaagcc aattcttcgt agttttttga atggatataa ttgcacagta cttgcctatg    420
gtgccactgg tgctgggaag acccacacta tgctaggatc agctgatgaa cctgagtga    480 tgtatctaac aatgttacac ctttacaaat gcatggatga gattaaagaa gagaaaatat    540
gtagtactgc agtttcatat ctggaggtat ataatgaaca gattcgtgat ctcttagtaa    600
attcagggcc acttgctgtc cgggaagata cccaaaaagg ggtggtcgtt catggactta    660
ctttacacca gcccaaatcc tcagaagaaa ttttacattt attggataat ggaaacaaaa    720
acaggacaca acatcccact gatatgaatg ccacatcttc tcgttctcat gctgttttcc    780
aaatttactt gcgacaacaa gacaaaacag caagtatcaa tcaaaatgtc cgtattgcca    840
agatgtcact cattgacctg gcaggatctg agcgagcaag tacttccggt gctaagggga    900
cccgatttgt agaaggcaca aatattaata gatcactttt agctcttggg aatgtcatca    960
atgccttagc agattcaaag agaaagaatc agcatatccc ttacagaaat agtaagctta   1020
ctcgcttgtt aaaggattct cttggaggaa actgtcaaac tataatgata gctgctgtta   1080
gtccttcctc tgtattctac gatgacacat ataacactct taagtatgct aaccgggcaa   1140
aggacattaa atcttctttg aagagcaatg ttcttaatgt caataatcat ataactcaat   1200
atgtaaagat ctgtaatgag cagaaggcag agattttatt gttaaaagaa aaactaaaag   1260

-continued

```
cctatgaaga acagaaagcc ttcactaatg aaaatgacca agcaaagtta atgatttcaa      1320
accctcagga aaaagaaatc gaaaggtttc aagaaatcct gaactgcttg ttccagaatc      1380
gagaagaaat tagacaagaa tatctgaagt tggaaatgtt acttaaagaa atgaacttaa      1440
aatcattcta ccaacaacag tgccataaac aaatagaaat gatgtgttct gaagacaaag      1500
tagaaaaggc cactggaaaa cgagatcata gacttgcaat gttgaaaact cgtcgctcct      1560
acctggagaa aaggagggag gaggaattga agcaatttga tgagaatact aattggctcc      1620
atcgtgtcga aaaagaaatg ggactcttaa gtcaaaacgg tcatattcca aaggaactca      1680
agaaagatct tcattgtcac catttgcacc tccagaacaa agatttgaaa gcacaaatta      1740
gacatatgat ggatctagct tgtcttcagg aacagcaaca caggcagact gaagcagtat      1800
tgaatgcttt acttccaacc ctaagaaaac aatattgcac attaaaagaa gccggcctgt      1860
caaatgctgc ttttgaatct gacttcaaag agatcgaaca tttggtagag aggaaaaaag      1920
tggtagtttg ggctgaccaa actggcgaac aaccaaagca aaacgatcta cccgggattt      1980
ctgttcttat gaccttttca caacttggac cagttcagcc tattccttgt tgctcatctt      2040
caggtggaac taatctggtt aagattccta cagaaaaaag aactcggaga aaactaatgc      2100
catctccctt gaaaggacag catactctaa agtctccacc atctcaaagt gtgcagctca      2160
atgattctct tagcaaagaa cttcagccta ttgtatatac accagaagac tgtagaaaag      2220
cttttcaaaa tccgtctaca gtaaccttaa tgaaaccatc atcatttact acaagttttc      2280
aggctatcag ctcaaacata aacagtgata attgtctgaa aatgttgtgt gaagtagcta      2340
tccctcataa tagaagaaaa gaatgtggac aggaggactt ggactctaca tttactatat      2400
gtgaagacat caagagctcg aagtgtaaat tacccgaaca agaatcacta ccaaatgata      2460
acaaagacat tttacaacgg cttgatcctt cttcattctc aactaagcat tctatgcctg      2520
taccaagcat ggtgccatcc tacatggcaa tgactactgc tgccaaaagg aaacggaaat      2580
taacaagttc tacatcaaac agttcgttaa ctgcagacgt aaattctgga tttgccaaac      2640
gtgttcgaca agataattca agtgagaagc acttacaaga aaacaaacca acaatggaac      2700
ataaaagaaa catctgtaaa ataaatccaa gcatggttag aaaatttgga agaaatattt      2760
caaaaggaaa tctaagataa atcacttcaa aaccaagcaa aatgaagttg atcaaatctg      2820
cttttcaaag tttatccaat acccttttcaa aaatatattt aaaatctttg aaagaagacc      2880
catcttaaag ctaagtttac ccaagtactt tcagcaagca gaaaaatgaa actctttgtt      2940
ttcttctttt gtgttctaaa aaaataaaat ttcaaaagaa aaggttgtct tttaagtttt      3000
ttaaatattt gttgcctttt aaaatccctg agtgtaagtt accatggtgg cagcttagtt      3060
ttactatgcc acaacaagtt gactaggaca ttttagtaaa tggtagtgag ttaaattatc      3120
tttattattt tttaaaaata agaatttaga agtggtaaaa ttatggccca agatgtattt      3180
ggttctctat tatgttttga tacattattt taatcatata tatgactttc cttttcaaaa      3240
atactttaat gtacaagtgt aaatatatgt gcccataaaa tcattgtaaa tattatttag      3300
tcatcacaaa taaaatattg tcccttgcta cttgatatat taaagatgta gattttaaag      3360
tgaaaaaaaa aaaaaaaaa                                                   3379
```

<210> SEQ ID NO 12
<211> LENGTH: 898
<212> TYPE: PRT
<213> ORGANISM: Homo sapiens

<400> SEQUENCE: 12

-continued

```
Met Ser Val Thr Glu Glu Asp Leu Cys His His Met Lys Val Val
1               5                   10                  15

Arg Val Arg Pro Glu Asn Thr Lys Glu Lys Ala Ala Gly Phe His Lys
            20                  25                  30

Val Val His Val Asp Lys His Ile Leu Val Phe Asp Pro Lys Gln
        35                  40                  45

Glu Glu Val Ser Phe Phe His Gly Lys Lys Thr Thr Asn Gln Asn Val
    50                  55                  60

Ile Lys Lys Gln Asn Lys Asp Leu Lys Phe Val Phe Asp Ala Val Phe
65                  70                  75                  80

Asp Glu Thr Ser Thr Gln Ser Glu Val Phe Glu His Thr Thr Lys Pro
                85                  90                  95

Ile Leu Arg Ser Phe Leu Asn Gly Tyr Asn Cys Thr Val Leu Ala Tyr
            100                 105                 110

Gly Ala Thr Gly Ala Gly Lys Thr His Thr Met Leu Gly Ser Ala Asp
        115                 120                 125

Glu Pro Gly Val Met Tyr Leu Thr Met Leu His Leu Tyr Lys Cys Met
    130                 135                 140

Asp Glu Ile Lys Glu Glu Lys Ile Cys Ser Thr Ala Val Ser Tyr Leu
145                 150                 155                 160

Glu Val Tyr Asn Glu Gln Ile Arg Asp Leu Leu Val Asn Ser Gly Pro
                165                 170                 175

Leu Ala Val Arg Glu Asp Thr Gln Lys Gly Val Val His Gly Leu
            180                 185                 190

Thr Leu His Gln Pro Lys Ser Ser Glu Glu Ile Leu His Leu Leu Asp
        195                 200                 205

Asn Gly Asn Lys Asn Arg Thr Gln His Pro Thr Asp Met Asn Ala Thr
    210                 215                 220

Ser Ser Arg Ser His Ala Val Phe Gln Ile Tyr Leu Arg Gln Gln Asp
225                 230                 235                 240

Lys Thr Ala Ser Ile Asn Gln Asn Val Arg Ile Ala Lys Met Ser Leu
                245                 250                 255

Ile Asp Leu Ala Gly Ser Glu Arg Ala Ser Thr Ser Gly Ala Lys Gly
            260                 265                 270

Thr Arg Phe Val Glu Gly Thr Asn Ile Asn Arg Ser Leu Leu Ala Leu
        275                 280                 285

Gly Asn Val Ile Asn Ala Leu Ala Asp Ser Lys Arg Lys Asn Gln His
    290                 295                 300

Ile Pro Tyr Arg Asn Ser Lys Leu Thr Arg Leu Leu Lys Asp Ser Leu
305                 310                 315                 320

Gly Gly Asn Cys Gln Thr Ile Met Ile Ala Ala Val Ser Pro Ser Ser
                325                 330                 335

Val Phe Tyr Asp Asp Thr Tyr Asn Thr Leu Lys Tyr Ala Asn Arg Ala
            340                 345                 350

Lys Asp Ile Lys Ser Ser Leu Lys Ser Asn Val Leu Asn Val Asn Asn
        355                 360                 365

His Ile Thr Gln Tyr Val Lys Ile Cys Asn Glu Gln Lys Ala Glu Ile
    370                 375                 380

Leu Leu Leu Lys Glu Lys Leu Lys Ala Tyr Glu Glu Gln Lys Ala Phe
385                 390                 395                 400

Thr Asn Glu Asn Asp Gln Ala Lys Leu Met Ile Ser Asn Pro Gln Glu
                405                 410                 415
```

-continued

```
Lys Glu Ile Glu Arg Phe Gln Glu Ile Leu Asn Cys Leu Phe Gln Asn
                420                 425                 430

Arg Glu Glu Ile Arg Gln Glu Tyr Leu Lys Leu Glu Met Leu Leu Lys
                435                 440                 445

Glu Asn Glu Leu Lys Ser Phe Tyr Gln Gln Cys His Lys Gln Ile
            450                 455                 460

Glu Met Met Cys Ser Glu Asp Lys Val Glu Lys Ala Thr Gly Lys Arg
465                 470                 475                 480

Asp His Arg Leu Ala Met Leu Lys Thr Arg Arg Ser Tyr Leu Glu Lys
                485                 490                 495

Arg Arg Glu Glu Glu Leu Lys Gln Phe Asp Glu Asn Thr Asn Trp Leu
                500                 505                 510

His Arg Val Glu Lys Glu Met Gly Leu Leu Ser Gln Asn Gly His Ile
            515                 520                 525

Pro Lys Glu Leu Lys Lys Asp Leu His Cys His His Leu His Leu Gln
530                 535                 540

Asn Lys Asp Leu Lys Ala Gln Ile Arg His Met Met Asp Leu Ala Cys
545                 550                 555                 560

Leu Gln Glu Gln Gln His Arg Gln Thr Glu Ala Val Leu Asn Ala Leu
                565                 570                 575

Leu Pro Thr Leu Arg Lys Gln Tyr Cys Thr Leu Lys Glu Ala Gly Leu
                580                 585                 590

Ser Asn Ala Ala Phe Glu Ser Asp Phe Lys Glu Ile Glu His Leu Val
            595                 600                 605

Glu Arg Lys Lys Val Val Trp Ala Asp Gln Thr Gly Glu Gln Pro
610                 615                 620

Lys Gln Asn Asp Leu Pro Gly Ile Ser Val Leu Met Thr Phe Ser Gln
625                 630                 635                 640

Leu Gly Pro Val Gln Pro Ile Pro Cys Cys Ser Ser Ser Gly Gly Thr
                645                 650                 655

Asn Leu Val Lys Ile Pro Thr Glu Lys Arg Thr Arg Arg Lys Leu Met
            660                 665                 670

Pro Ser Pro Leu Lys Gly Gln His Thr Leu Lys Ser Pro Pro Ser Gln
            675                 680                 685

Ser Val Gln Leu Asn Asp Ser Leu Ser Lys Glu Leu Gln Pro Ile Val
            690                 695                 700

Tyr Thr Pro Glu Asp Cys Arg Lys Ala Phe Gln Asn Pro Ser Thr Val
705                 710                 715                 720

Thr Leu Met Lys Pro Ser Ser Phe Thr Thr Ser Phe Gln Ala Ile Ser
                725                 730                 735

Ser Asn Ile Asn Ser Asp Asn Cys Leu Lys Met Leu Cys Glu Val Ala
            740                 745                 750

Ile Pro His Asn Arg Arg Lys Glu Cys Gly Gln Glu Asp Leu Asp Ser
            755                 760                 765

Thr Phe Thr Ile Cys Glu Asp Ile Lys Ser Ser Lys Cys Lys Leu Pro
            770                 775                 780

Glu Gln Glu Ser Leu Pro Asn Asp Asn Lys Asp Ile Leu Gln Arg Leu
785                 790                 795                 800

Asp Pro Ser Ser Phe Ser Thr Lys His Ser Met Pro Val Pro Ser Met
                805                 810                 815

Val Pro Ser Tyr Met Ala Met Thr Thr Ala Ala Lys Arg Lys Arg Lys
            820                 825                 830

Leu Thr Ser Ser Thr Ser Asn Ser Ser Leu Thr Ala Asp Val Asn Ser
```

-continued

```
            835                 840                 845
Gly Phe Ala Lys Arg Val Arg Gln Asp Asn Ser Ser Glu Lys His Leu
    850                 855                 860

Gln Glu Asn Lys Pro Thr Met Glu His Lys Arg Asn Ile Cys Lys Ile
865                 870                 875                 880

Asn Pro Ser Met Val Arg Lys Phe Gly Arg Asn Ile Ser Lys Gly Asn
                885                 890                 895

Leu Arg
```

US 7,829,296 B2

KINESIN POLYPEPTIDES, POLYNUCLEOTIDES ENCODING SAME AND COMPOSITIONS AND METHODS OF USING SAME

RELATED APPLICATIONS

This Application is a National Phase of PCT Patent Application No. PCT/IL2006/000506 having International Filing Date of Apr. 25, 2006, which claims the benefit of U.S. Provisional Patent Application No. 60/674,293 filed on Apr. 25, 2005. The contents of the above Applications are all incorporated herein by reference.

FIELD AND BACKGROUND OF THE INVENTION

The present invention relates to novel kinesin polypeptides, polynucleotides encoding same, pharmaceutical compositions and uses thereof.

Kinesins are motor proteins that play a role in intracellular positioning and trafficking of intracellular components, mRNA and protein. These cytoskeleton-dependent motor proteins have been implicated in both gene expression and cell differentiation. Their associated molecular motor action is based on hydrolysis of ATP to produce force and movement along microtubules.

Structurally, kinesins consist of three functional parts: a motor domain that reversibly binds microtubules and converts chemical energy into the motion; a central helical coiled coil domain, which possesses protein-protein interactions; and a tail, which interacts with cargo and regulates the motor activity. The motor domain comprises a signature of 340 amino acid residues that transduces ATP hydrolysis into directed movement along a microtubule. The specificity of the interaction of kinesins with their cargo is determined by their tail domains, which are divergent from one another. Although more than 50 kinesin proteins have been identified only a few of their specific cargos are known. For example, KIF13A binds cargo vesicles of AP-1 and mannose-6-phosphate receptor (M6PR). KIF17 was shown to interact with the PDZ domain of sorting protein mLin-10 (Mint1/X11), which is a component of a large complex that includes mLin-2 (CASK), mLin-7 MALS/Velis and the transmembrane protein NR2B, a subunit of the N-methyl-D-aspartate (NMDA) receptor.

Estrogens are an important class of steroidal hormones that stimulate the development and maintenance of fundamental sexual characteristics in humans. In addition, estrogens have been demonstrated to affect a variety of diverse biological processes. Many of the incidental effects of estrogens are positive, including the maintenance of bone density, central nervous system function and preservation of memory. However, estrogens also have been demonstrated to have serious negative effects, including promoting the development of breast and endometrial cancers.

The estrogen effect on cellular metabolism is mediated by two receptors—ERα and ERβ which belong to the steroid nuclear receptor superfamily. The receptor consists of several domains. The A/B domain at the N-terminus encodes the ligand-independent activation function domain (AF1). This is responsible for protein-protein interactions. The DNA-binding domain (DBD) mediates receptor binding to promoters of estrogen-regulated genes. Region D is a flexible hinge region between DNA and the ligand-binding domains (LBD). The C-terminal consists of the AF-2 domain, which is involved in interactions with transcriptional co-activators via nuclear receptor boxes comprising LXXLL-motifs.

ERα is expressed by two splice forms; the 66 kDa and the 46 kDa, which lacks the AF-1 domain. The estrogen receptor binds its ligand in the cytoplasm and is then translocated to the nucleus. The receptor binds to genes comprising estrogen response elements (ERE) or to transcription factors such as AP-1 and SP1 thereby regulating other genes.

The nuclear signaling of estrogen occurs within 30-60 minutes following hormonal treatment. An alternative rapid (seconds to minutes) pathway is activation of Mitogen Activated Protein Kinases (MAPKs) such as p38 and ERK1/2. This leads to an increase in cAMP or Inositol 1,4,5-trisphosphate (IP3), both of which are mediators of the non-genomic actions of estrogen.

The estrogen receptor (ER) is localized to different cellular compartments, including the cell membrane, cytoplasm, and nucleus and it is known to shuttle dynamically in the cell. Various mechanisms have been proposed to explain how proteins in general and receptors specifically translocate in a cell. In this regard it has been suggested that kinesin may play a role in intracellular protein shuttling. As yet, no kinesin has been shown to bind to the estrogen receptor.

Due to estrogen's far-reaching effects, there is a widely recognized need for, and it would be highly advantageous to have, novel estrogen receptor modulators.

SUMMARY OF THE INVENTION

According to one aspect of the present invention there is provided an isolated polynucleotide comprising a nucleic acid sequence encoding a KIF18A polypeptide, the polypeptide being expressed in mesenchymal stem cells.

According to another aspect of the present invention there is provided an isolated polynucleotide as set forth in SEQ ID NO: 1 or SEQ ID NO: 3.

According to yet another aspect of the present invention there is provided an oligonucleotide capable of specifically hybridizing to an isolated polynucleotide as set forth in SEQ ID NO:1 and not to an isolated polynucleotide as set forth in SEQ ID NO: 11.

According to still another aspect of the present invention there is provided an oligonucleotide capable of specifically hybridizing to an isolated polynucleotide as set forth in SEQ ID NO:3 and not to an isolated polynucleotide as set forth in SEQ ID NO: 11.

According to an additional aspect of the present invention there is provided an isolated polypeptide comprising an amino acid sequence encoding a KIF18A polypeptide, the polypeptide being expressed in mesenchymal stem cells.

According to yet an additional aspect of the present invention there is provided an isolated polypeptide as set forth in SEQ ID NO: 2.

According to still an additional aspect of the present invention there is provided an antibody comprising an antigen recognition domain capable of specifically recognizing the isolated polypeptide comprising an amino acid sequence encoding a KIF18A polypeptide, the polypeptide being expressed in mesenchymal stem cells, and not to an isolated polypeptide as set forth in SEQ ID NO: 12.

According to a further aspect of the present invention there is provided a method of modulating estrogen signaling in a cell, comprising contacting the cell with an agent capable of regulating an expression and/or activity of the polypeptide comprising an amino acid sequence encoding a KIF18A polypeptide, the polypeptide being expressed in mesenchymal stem cells, thereby modulating estrogen signaling in the cell.

According to yet a further aspect of the present invention there is provided a method of modulating estrogen signaling in a cell, comprising contacting the cell with an agent capable of regulating an expression and/or activity of the polypeptide as set forth in SEQ ID NO: 2, thereby modulating estrogen signaling in the cell.

According to still a further aspect of the present invention there is provided a pharmaceutical composition comprising as an active ingredient the polypeptide comprising an amino acid sequence encoding a KIF18A polypeptide, the polypeptide being expressed in mesenchymal stem cells, and a pharmaceutically acceptable carrier.

According to still a further aspect of the present invention there is provided a pharmaceutical composition comprising as an active ingredient the polypeptide as set forth in SEQ ID NO: 2, and a pharmaceutically acceptable carrier.

According to still a further aspect of the present invention there is provided a pharmaceutical composition comprising as an active ingredient an agent capable of down-regulating an expression and/or activity of the isolated polypeptide comprising an amino acid sequence encoding a KIF18A polypeptide, the polypeptide being expressed in mesenchymal stem cells, and a pharmaceutically acceptable carrier.

According to still a further aspect of the present invention there is provided a nucleic acid construct, comprising the polynucleotide comprising a nucleic acid sequence encoding a KIF18A polypeptide, the polypeptide being expressed in mesenchymal stem cells.

According to still a further aspect of the present invention there is provided a pharmaceutical composition comprising as an active ingredient the polynucleotide comprising a nucleic acid sequence encoding a KIF18A polypeptide, the polypeptide being expressed in mesenchymal stem cells and a pharmaceutically acceptable carrier.

According to still a further aspect of the present invention there is provided a method of treating infertility, the method comprising administering to a subject in need thereof a therapeutically effective amount of a KIF18A polypeptide, thereby treating infertility.

According to still a further aspect of the present invention there is provided a method of identifying a mesenchymal stem cell comprising identifying in a biological sample a cell expressing the polynucleotide comprising a nucleic acid sequence encoding a KIF18A polypeptide, the polypeptide being expressed in mesenchymal stem cells, the cell being the mesenchymal stem cell.

According to still a further aspect of the present invention there is provided a method of identifying a mesenchymal stem cell comprising identifying in a biological sample a cell expressing the isolated polynucleotide as set forth in SEQ ID NO: 1 or SEQ ID NO: 3, the cell being the mesenchymal stem cell.

According to still a further aspect of the present invention there is provided a method of identifying a mesenchymal stem cell comprising identifying in a biological sample a cell expressing the polypeptide comprising an amino acid sequence encoding a KIF18A polypeptide, the polypeptide being expressed in mesenchymal stem cells, the cell being the mesenchymal stem cell.

According to still a further aspect of the present invention there is provided a method of identifying a mesenchymal stem cell comprising identifying in a biological sample a cell expressing the polypeptide as set forth in SEQ ID NO: 2, the cell being the mesenchymal stem cell.

According to further features in preferred embodiments of the invention described below, the polypeptide is capable of binding an estrogen receptor.

According to still further features in the described preferred embodiments, the polypeptide is expressed in testis cells.

According to still further features in the described preferred embodiments, the estrogen receptor is ERα.

According to still further features in the described preferred embodiments, the estrogen receptor is ERβ.

According to still further features in the described preferred embodiments, the nucleic acid sequence is as set forth in SEQ ID NO: 1 or SEQ ID NO: 3.

According to still further features in the described preferred embodiments, the nucleic acid sequence is at least 90% identical to a sequence as set forth in SEQ ID NO: 1 or SEQ ID NO: 3.

According to still further features in the described preferred embodiments, the KIF18A polypeptide comprises an amino acid sequence being 90% homologous to SEQ ID NO: 2.

According to still further features in the described preferred embodiments, the amino acid sequence is as set forth in SEQ ID NO: 2.

According to still further features in the described preferred embodiments, the isolated polypeptide comprising an amino acid sequence encoding a KIF18A polypeptide, the polypeptide being expressed in mesenchymal stem cells, is expressed in testis cells.

According to still further features in the described preferred embodiments, the isolated polypeptide comprising an amino acid sequence encoding a KIF18A polypeptide, the polypeptide being expressed in mesenchymal stem cells, is capable of binding an estrogen receptor.

According to still further features in the described preferred embodiments, the regulating is down-regulating.

According to still further features in the described preferred embodiments, the agent is selected from the group consisting of an antibody, an antisense, an siRNA, a ribozyme and a DNAzyme.

According to still further features in the described preferred embodiments, the agent comprises the oligonucleotide capable of specifically hybridizing to an isolated polynucleotide as set forth in SEQ ID NO:1 and not to an isolated polynucleotide as set forth in SEQ ID NO: 11.

According to still further features in the described preferred embodiments, the agent comprises the oligonucleotide capable of specifically hybridizing to an isolated polynucleotide as set forth in SEQ ID NO:3 and not to an isolated polynucleotide as set forth in SEQ ID NO: 11.

According to still further features in the described preferred embodiments, the agent comprises an antibody comprising an antigen recognition domain capable of specifically recognizing the isolated polypeptide comprising an amino acid sequence encoding a KIF18A polypeptide, the polypeptide being expressed in mesenchymal stem cells and not to an isolated polypeptide as set forth in SEQ ID NO: 12.

According to still further features in the described preferred embodiments, the regulating is up-regulating.

According to still further features in the described preferred embodiments, the agent is the isolated polynucleotide comprising a nucleic acid sequence encoding a KIF18A polypeptide, the polypeptide being expressed in mesenchymal stem cells.

According to still further features in the described preferred embodiments, the agent is the isolated polynucleotides as set forth in SEQ ID NO: 1 or SEQ ID NO: 3.

According to still further features in the described preferred embodiments, the agent is the isolated polypeptide comprising an amino acid sequence encoding a KIF18A polypeptide, the polypeptide being expressed in mesenchymal stem cells.

According to still further features in the described preferred embodiments, the agent is the isolated polypeptide as set forth in SEQ ID NO: 2.

According to still further features in the described preferred embodiments, the cell is a mesenchymal stem cell or a testes cell.

According to still further features in the described preferred embodiments, the contacting is effected in vivo.

According to still further features in the described preferred embodiments, the contacting is effected ex vivo.

According to still further features in the described preferred embodiments, the KIF18A polypeptide is the isolated polypeptide comprising an amino acid sequence encoding a KIF18A polypeptide, the polypeptide being expressed in mesenchymal stem cells.

According to still further features in the described preferred embodiments, the KIF18A polypeptide is the isolated polypeptide as set forth in SEQ ID NO: 2.

According to still further features in the described preferred embodiments, the identifying is effected via the oligonucleotide capable of specifically hybridizing to an isolated polynucleotide as set forth in SEQ ID NO:1 and not to an isolated polynucleotide as set forth in SEQ ID NO: 11.

According to still further features in the described preferred embodiments, the identifying is effected via the oligonucleotide capable of specifically hybridizing to an isolated polynucleotide as set forth in SEQ ID NO:3 and not to an isolated polynucleotide as set forth in SEQ ID NO: 11.

According to still further features in the described preferred embodiments, the identifying is effected via the antibody comprising an antigen recognition domain capable of specifically recognizing the isolated polypeptide comprising an amino acid sequence encoding a KIF18A polypeptide, the polypeptide being expressed in mesenchymal stem cells and not to an isolated polypeptide as set forth in SEQ ID NO: 12.

The present invention successfully addresses the shortcomings of the presently known configurations by providing novel kinesins capable of binding estrogen receptors.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1A is a PCR amplification of MS-KIF18A cDNA (SEQ ID NO: 1), separated on a 1% agarose gel and visualized with ethidium bromide. FIG. 1B is a Northern blot of mesenchymal stem cells analyzed with a probe specific for MS-KIF18A (SEQ ID NO: 1)

FIG. 2A shows the largest open reading frame (ORF) of MS-KIF18A cDNA. FIG. 2B shows the number of base pairs in each of the 17 exons in MS-KIF18A cDNA.

FIG. 5A identifies the presence of MS-KIF18A in cell lysates of mesenchymal stem cells (lane 1) and MBA-15 cells (lane 2) with anti-MS-KIF18A antibody. FIG. 5B identifies the presence of MS-KIF18A in cell lysates of COS-7 cells transfected with pcDNA3.1-His-tag-MS-KIF18A and blotted with anti-KIF18A (lane 2) and anti-His-tag (lane 1) antibodies.

FIG. 6A is schematic illustration of MS-KIF18A as compared to KOG0242 and a conserved motor domain region (KISc). KOG0242 (euKaryotic Orthologous Group) is a cluster of kinesin motor domain previously identified using a protein blast algorithm. (http://pstiing.licr.org/search.jsp?script=c_Homolog_info&querystring=KOG0242&linkscript=search.jsp). FIG. 6B is a sequence alignment scheme of MS-KIF18A motor domain with other kinesin motor domains.

FIG. 7A is a sequence alignment of MS-KIF18A and conventional kinesin (KISc). Conventional kinesin consists of two heavy chains (KHC) which are usually supplemented with two light chains (KLC) that participate in cargo binding. The heavy chain comprises an N-terminal motor domain including the core motor domain and the neck linker, a central neck and stalk domain which is mostly α-helical, and a C-terminal tail domain which binds to the light chains and/or the cargo. The motor domain with the neck linker has a length of about 340 amino acids and contains the major microtubule binding elements as well as the ATPase catalytic site. FIG. 7B illustrates three-dimensional motor domain modeling of MS-KIF18A (purple) to the conventional kinesin motor domain structure (Blue), microtubule-binding site (White) and ATP-binding site (red).

FIG. 8A illustrates the position of the motifs on the amino acid sequence of MS-KIF18A polypeptide. Motor domain (italic), coiled coil region (underlined), ATPase site amino acids (black box), microtubule binding site (grey box), LXXLL motifs (bold italic), ΦXXΦΦ-like motifs (double underlined) and nuclear localization signals (NLS—illustrated by bold black). FIG.

8B is a schematic illustration of the secondary structure of KIF18A, center region demonstrates the alpha-helical coiled coil structure.

Figure 9:
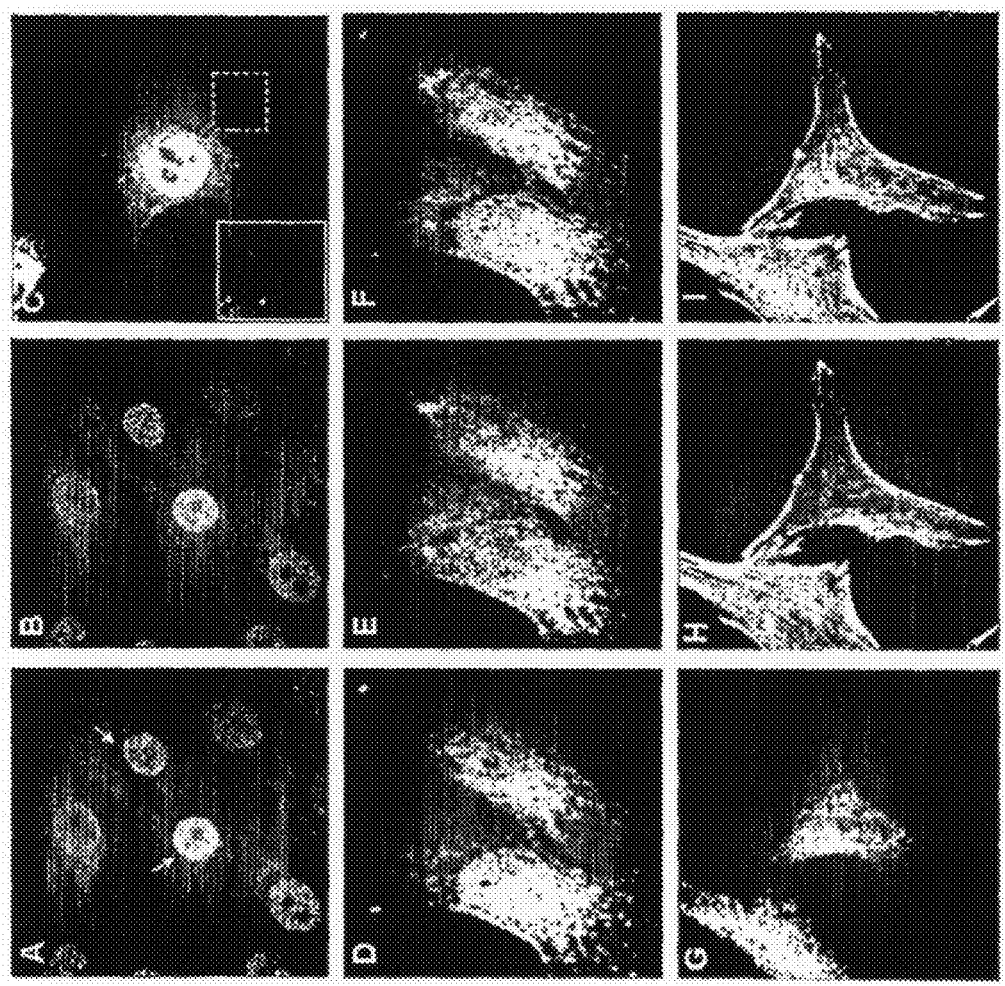

FIGS. 9A-I are photomicrographs illustrating the intracellular localization of MS-KIF18A in MBA-15 cells. Cells were stained with anti-MS-KIF18A-Texas Red (FIG. 9A) and DAPI, overlay image (FIG. 9B). At higher magnification, it can be seen that MS-KIF18A localizes to the plasma ruffles (FIG. 9C). Co-localization with tubulin was visualized in cells stained with anti-MS-KIF18A-Rhodamine (FIG. 9D) and anti-tubulin-FITC (FIG. 9E), overlay image (FIG. 9F). Co-localization with actin was visualized in cells stained with Anti-MS-KIF18A-FITC (FIG. 9G) and Phalloidine-actin (FIG. 9H) and overlay image (FIG. 9I).

Figure 10:
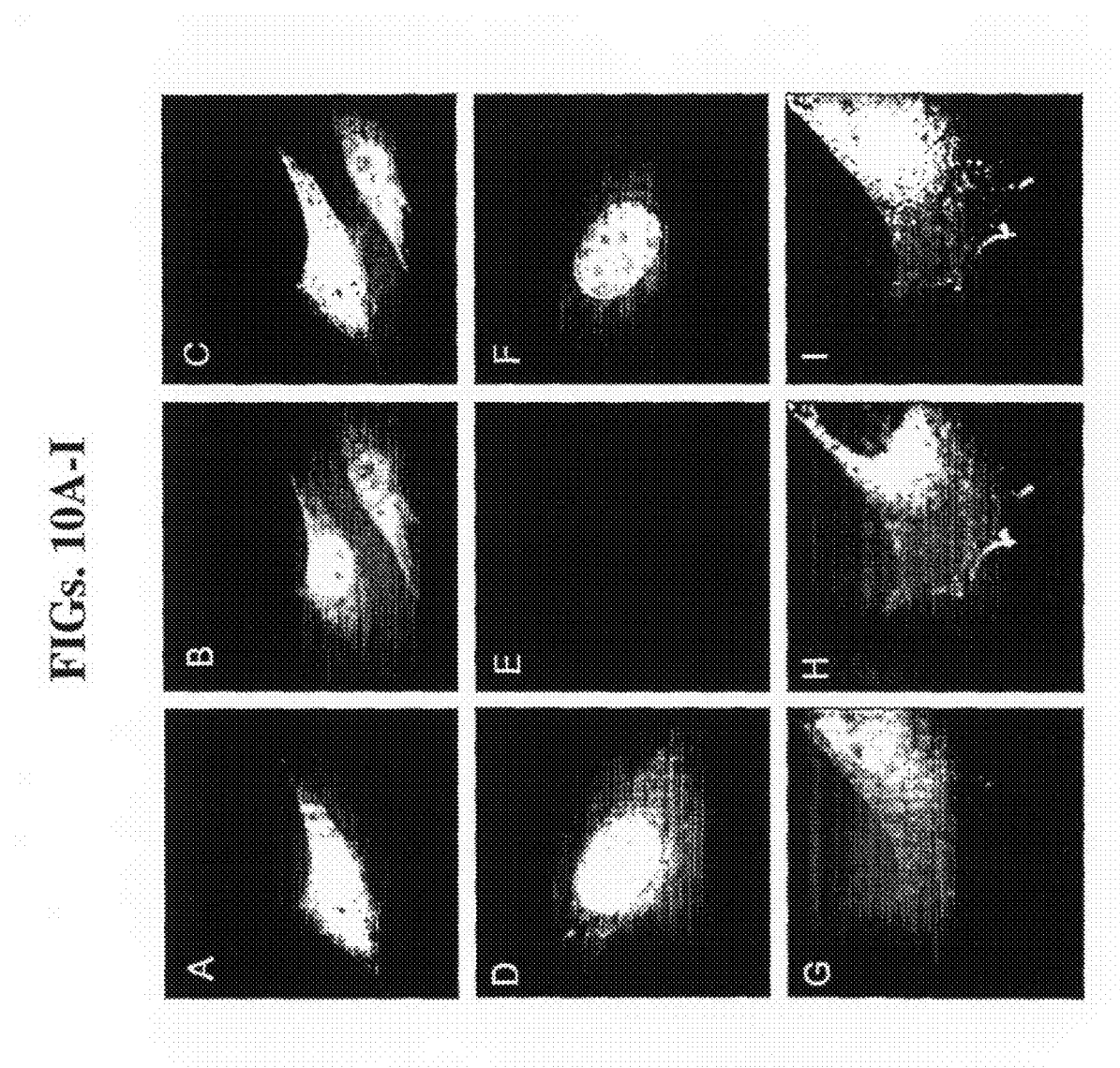

FIGS. 10A-I are photomicrographs illustrating the intracellular localization of EGFP-MS-KIF18A transfected in MBA-15 cells. Transiently transfected cells with EGFP-MS-KIF18A (FIGS. 10A, 10D and 10G), were stained with anti-MSKIF18A antibody (Texas Red) (FIG. 10B), anti Lamin B (FITC) (FIG. 10E), or co-transfected with pCMV-IL-2R and stained with anti-IL-2R (FIG. 10H), Overlay images are illustrated in FIGS. 10C, 10F and 10I.

Figure 11:
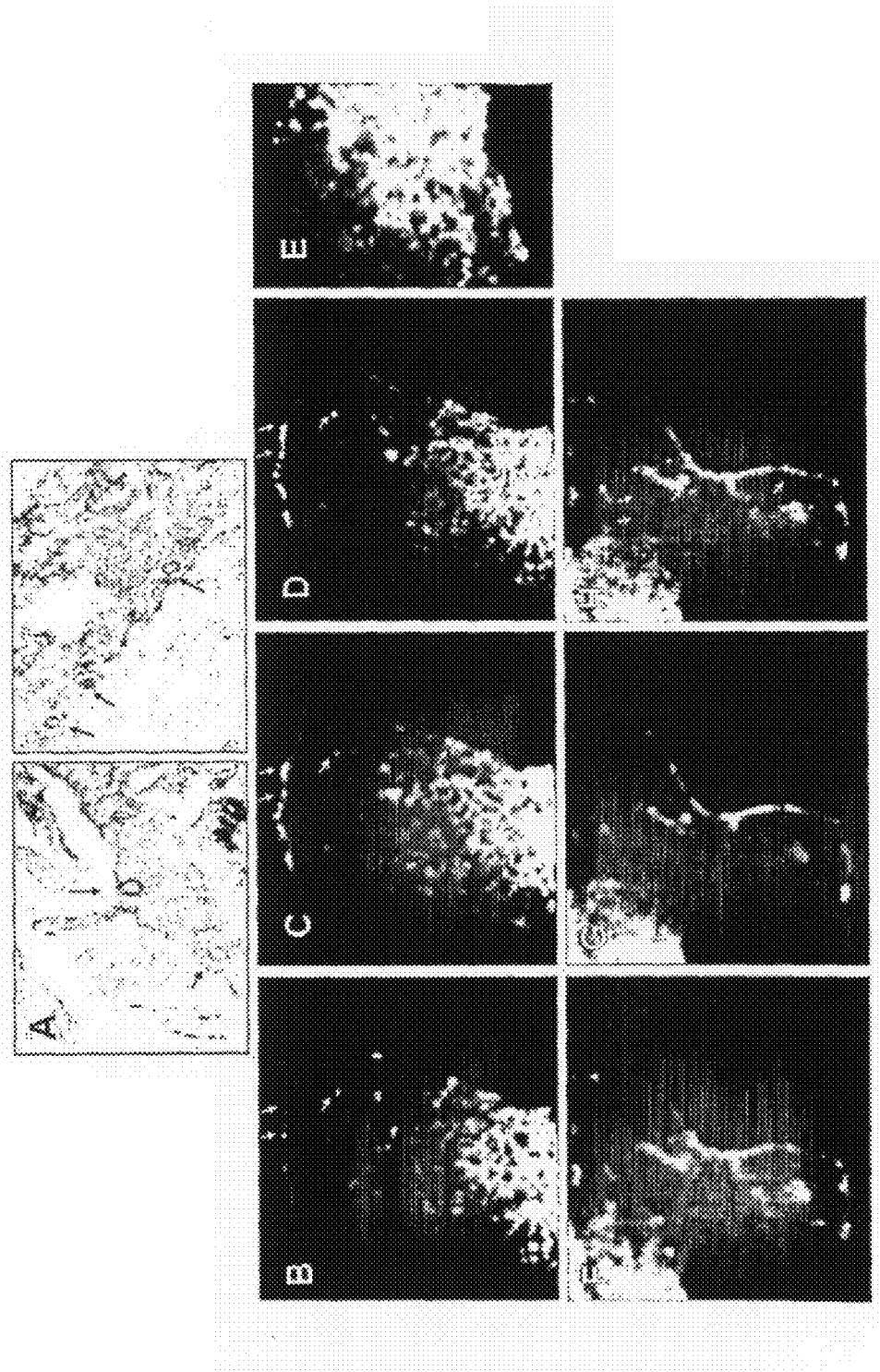

FIGS. 11A-H are photomicrographs illustrating the intracellular localization of EGFP-MS-KIF18A and calveloin-1. FIG. 11A is a transmission electron microscopy micrograph of MBA-15 cells illustrating the caveolae structures at the plasma membrane region (arrows). Colocalization of MS-KIF18A and caveolin-1 is illustrated by immunofluorescent photomicrographs (FIGS. 11B-H). MBA-15 cells were stained with anti-MS-KIF18A (FITC) (FIGS. 11B and 11F), anti-caveolin-1 (Texas Red) (C, G) overlay image (FIGS. 11D, 11E and 11H).

Figure 12:
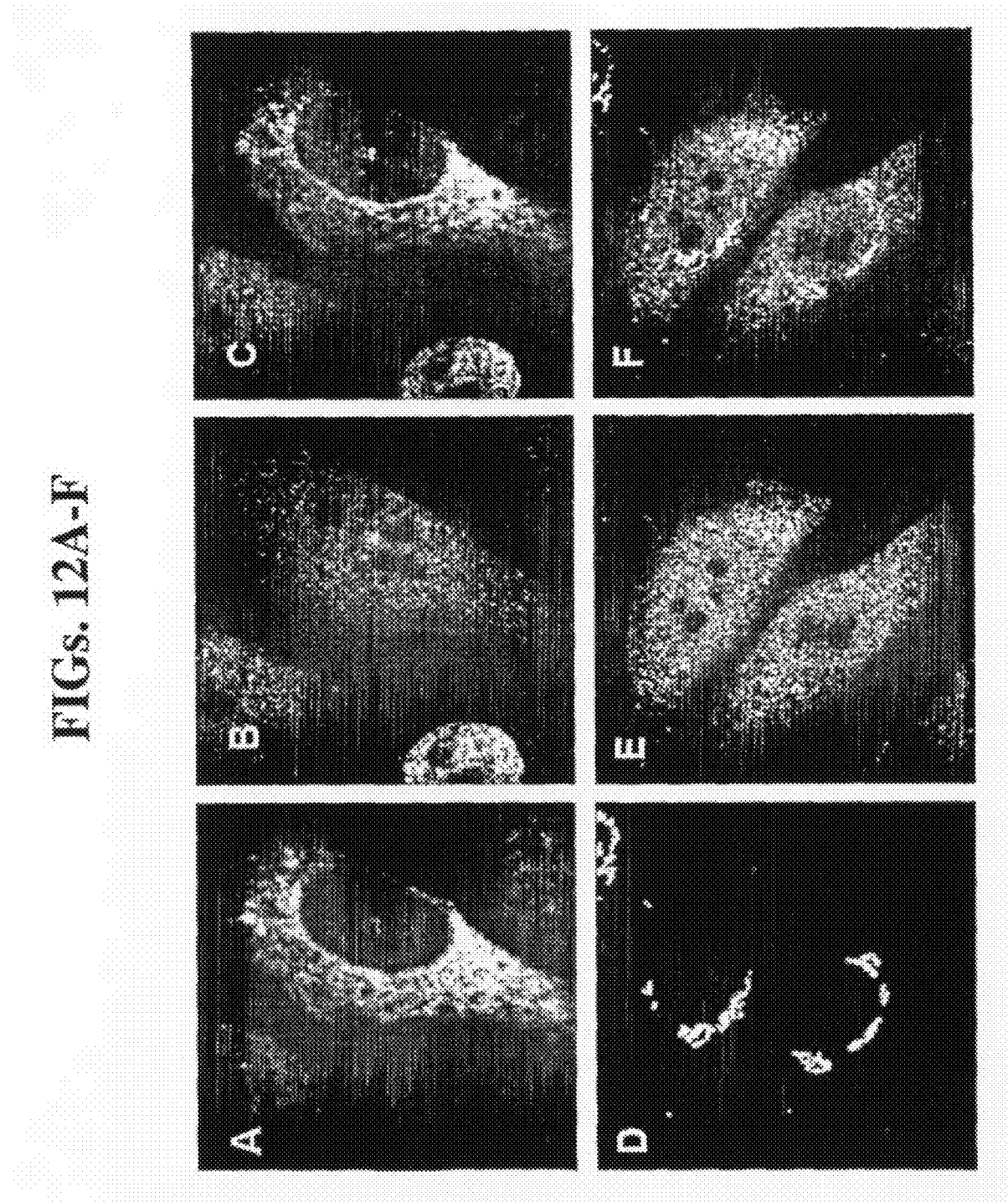

FIGS. 12A-F are photomicrographs illustrating the intracellular localization of EGFP-MS-KIF18A as related to Golgi complex and endoplasmic reticulum. MBA-15 cells were stained with anti-MS-KIF18A (Texas Red) (FIGS. 12B and 12E), with anti-KDEL receptor (FITC) for endoplasmic reticulum (FIG. 12A) or with anti-GM130, Golgi matrix protein (FITC) (FIG. 12D). Overlay images (FIGS. 12C and 12F).

Figure 13:
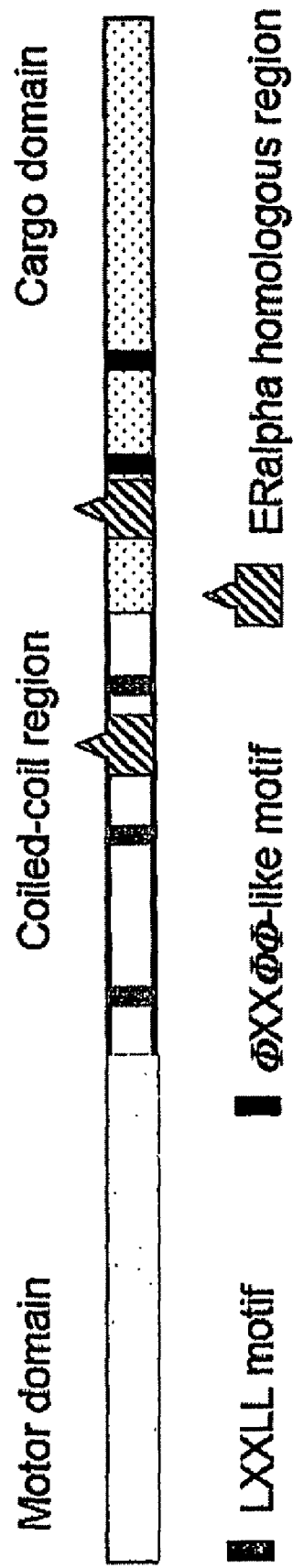

FIG. 13 is a schematic presentation of MSKIF-18A putative interaction motifs.

FIGS. 14A-B illustrate analyses of MS-KIF18A and ERα association in transfected COS-7 cells. His-MS-KIF18A and ERα 66KD were co-transfected into COS-7 cells and analyzed for the protein interactions. (Lane 1) Whole cells lysate from non-transfected and (Lane 3) whole lysate from ERα66 transfected cells. Immunoprecipitation with beads only (Lane 2), with anti-His (Lane 4) anti-MS-KIF18A (Lane 5) Western blot was performed with anti-ER (FIG. 14A) and anti-His-Tag (FIG. 14B) antibodies.

FIG. 15 illustrates analyses of MS-KIF18A and ERα association in endogenous expressed proteins in MBA-15 cells. Endogenous expressed MS-KIF18A and estrogen receptor were analyzed on immunoprecipitates from MBA-15 cells using anti-MS-KIF18A and detected by Western blot analysis with anti-ERα (lane 1) SRA-1010, (lane 2) AER311 or anti-MS-KIF18A (lower panels). Western blot with anti-ERα antibodies revealed association of various splice forms that were immunoprecipitated with MS-KIF18A (arrows).

FIGS. 16A-E illustrate analyses of MBA-15 cells following estrogen (17βE2) treatment. MBA-15 cells were treated with 17βE2 for 5 minutes in the presence of PD98059 (PD) (lane 2), or ICI 182,780 (ICI) (lane 3). Cells treated with 17βE2 only (lane 4) and cells not treated with 17βE2 (lane 1) were used as controls. FIG. 16A illustrates a western blot measured for p-ERK1/2 expression on whole cells lyses. Following immunoprecipitation with anti-MS-KIF18A, proteins were analyzed with ERα (FIG. 16B), MS-KIF18A (FIG. 16C) or pERK (FIG. 16D). pERK levels were quantified and presented by bar graph (FIG. 16E) which summarized three independent experiments; control compared to ICI+E (*p<0.05), control compared to PD98059 (**p<0.005).

DESCRIPTION OF THE PREFERRED EMBODIMENTS

The present invention is of novel KIF18A polypeptides, polynucleotides, compositions comprising same and uses thereof which are expressed in mesenchymal stromal cells.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Kinesins are motor proteins that play a role in intracellular positioning and trafficking of intracellular components, mRNA and protein. These cytoskeleton-dependent motor proteins have been implicated in both gene expression and cell differentiation. Their associated molecular motor action is based on hydrolysis of ATP to produce force and movement along microtubules.

Structurally, kinesins consist of three functional parts: a motor domain that reversibly binds microtubules and converts chemical energy into the motion; a central helical coiled coil domain, which possesses protein-protein interactions; and a tail, which interacts with cargo and regulates the motor activity. The motor domain comprises a signature of 340 amino acid residues that transduces ATP hydrolysis into directed movement along a microtubule. The specificity of the interaction of kinesins with their cargo is determined by their tail domains, which are divergent from one another. Although more than 50 kinesin proteins have been identified only a few of their specific cargos are known.

While reducing the present invention to practice the present inventor has uncovered novel alternatively spliced isoforms of the kinesin family member 18A (KIF18A) gene which are expressed in mesenchymal stem cells. Such isoforms have been named MS-KIF18A, since as opposed to previously cloned KIF18A transcripts they show an MSC pattern of expression. The present inventor has shown that MS-KIF18A is localized to the cell nucleus, the cell membrane and is also present in the cytoplasm of mesenchymal stem cells (FIGS. 9-12) suggesting a role for this kinesin in shuttling a cargo protein from the cytoplasm to the nucleus or vice versa. Furthermore, the present inventor has revealed that these isoforms are capable of binding to an estrogen receptor (FIGS. 14A-B and FIG. 15). Without being bound by theory, it is suggested that the novel kinesin polypeptides of the present invention interact with ER upon estrogen binding and mediate its transfer to the nucleus, suggesting its positive role in ER signaling. Thus, KIF18A polypeptides of the present invention may be used for modulating estrogen signaling.

Thus, according to one aspect of the present invention, there is provided an isolated polynucleotide comprising a nucleic acid sequence encoding a KIF18A polypeptide, being expressed in mesenchymal stem cells.

As used herein the phrase "KIF18A polypeptide" refers to a polypeptide expression product of the KIF18A gene (Genebank Accession No. NC_000011: c28086223-27998742).

As mentioned, the isolated polynucleotide of this aspect of the present invention is expressed in mesenchymal stem cells (MSCs). It will be appreciated that prior art isoforms of KIF18A are not expressed in MSCs.

As used herein, the phrase "mesenchymal stem cells" refers to bone marrow, non-hematopoietic pluripotent stem cells, also referred to as stromal cells. The cells may be either isolated or non-isolated and situated either in vivo or ex vivo.

As used herein the phrase "an isolated polynucleotide" refers to a single or double stranded nucleic acid sequences which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

The polynucleotides of the present invention are typically splice variants of the KIF18A gene.

The phrase "splice variant" refers to alternative forms of RNA transcribed from a KIF18A gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a polypeptide encoded by a splice variant of an mRNA transcribed from a gene.

The polynucleotides of the present invention may also be allelic variants of the sequence as set forth in GenBank Accession No. NC_000011: c28086223-27998742.

The phrase "allelic variant" refers to two or more alternative forms of a KIF18A gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

Examples of the isolated polynucleotides of the present invention are set forth in SEQ ID NO: 1 and SEQ ID NO: 3.

It will be appreciated that homologues of the sequences described hereinabove are also envisaged by the present invention. Accordingly, the polynucleotides of this aspect of the present invention may have a nucleic acid sequence at least 50%, at least 55%, at least 60%, at least 65%, at least 70%, at least 75%, at least 80%, at least 85%, at least 87%, at least 89%, at least 90% at least 91%, at least 93%, at least 95% or more say 100% identical to SEQ ID NO: 1 or 3, as determined using BlastN software of the National Center of Biotechnology Information (NCBI) using default parameters.

Thus, the present invention encompasses nucleic acid sequences described hereinabove; fragments thereof, sequences hybridizable therewith, sequences homologous thereto, sequences encoding similar polypeptides with different codon usage, altered sequences characterized by mutations, such as deletion, insertion or substitution of one or more nucleotides, either naturally occurring or man induced, either randomly or in a targeted fashion.

Since the polynucleotide sequences of the present invention encode previously unidentified polypeptides, the present invention also encompasses novel polypeptides or portions thereof, which are encoded by the isolated polynucleotides and respective nucleic acid fragments thereof described hereinabove.

Thus, the present invention also encompasses polypeptides encoded by the polynucleotide sequences of the present invention. An exemplary amino acid sequence of a polypeptide of the present invention is set forth in SEQ ID NO: 2.

The present invention also encompasses homologues of these polypeptides, such homologues can be at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% homologous to SEQ ID NO: 2.

The present invention also encompasses fragments of the above described polypeptides and polypeptides having mutations, such as deletions, insertions or substitutions of one or more amino acids, either naturally occurring or man induced, either randomly or in a targeted fashion.

As mentioned hereinabove the polypeptides of the present invention are typically capable of binding estrogen receptors.

As used herein, the phrase "estrogen receptor" refers to ER-α and/or ER-β (GenBank Accession Nos. NM_000125.2 and NM_001437, respectively).

Amino acid sequence information of the polypeptides of the present invention can be used to generate antibodies, which bind to the polypeptides of the present invention.

Thus, according to another aspect of the present invention there is provided an antibody comprising an antigen recognition domain capable of specifically recognizing the isolated polypeptide of the present invention and not to an isolated polypeptide as set forth in SEQ ID NO: 12

For example, antibodies may be directed to amino acid sequence coordinates 620-640 of SEQ ID NO: 2. This peptide comprises unique amino acid substitutions of the polypeptide variants of the present invention (positions 621, 639) which are not present in other KIF18A polypeptides, such as NP_112494 (SEQ ID NO:12).

Alternatively, antibodies may be directed to amino acid sequences which are present in all KIF18A polypeptides and not to other kinesin polypeptides, such as SEQ ID NO: 10. Such sequence coordinates represent a highly conserved sequence in all KIF18A polypeptides. Due to high sequence homology in this amino acid sequence region, such antibodies are expected to be cross-reactive to other variant polypeptides of the present invention. Accordingly, such antibodies may be useful for identifying novel variant polypeptides of the present invention by immunocloning an expression library of human mesenchymal stem cells as further described hereinbelow.

Specific peptides chosen for antibody generation are preferably selected immunogenic (i.e., capable of stimulating an antibody response). Parameters for testing peptide immunogenicity are well known in the art including, but not limited to, foreginess, molecular size, chemical composition and heterogeneity and susceptibility to antigen processing and presentation. Various sequence analysis software applications are known in the art, which provide an immunogenicity index according to, for example, the Jameson-Wolf algorithm. Examples include, but are not limited to, Sciprot (available from wwwdotasiaonlinedotnetdothk/-twcbio/DOCS/1/scPrteindothtm) and Macvector (available from wwwdotaccelrysdotcom/products/macvector/) as well as the widely utilized GCG package (Genetics Computer Group, Wisconsin).

The term "antibody" as used in this invention includes whole antibody molecules as well as functional fragments thereof, such as Fab, F(ab')$_2$, and Fv that are capable of binding with antigenic portions of the target polypeptide. These functional antibody fragments constitute preferred embodiments of the present invention, and are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule as described in, for example, U.S. Pat. No. 4,946,778.

Methods of generating such antibody fragments are well known in the art. (See for example, Harlow and Lane, Antibodies: A Laboratory Manual, Cold Spring Harbor Laboratory, New York, 1988, incorporated herein by reference).

Purification of serum immunoglobulin antibodies (polyclonal antisera) or reactive portions thereof can be accomplished by a variety of methods known to those of skill in the art including, precipitation by ammonium sulfate or sodium sulfate followed by dialysis against saline, ion exchange chromatography, affinity or immunoaffinity chromatography as well as gel filtration, zone electrophoresis, etc. (see Goding in, Monoclonal Antibodies: Principles and Practice, 2nd ed., pp. 104-126, 1986, Orlando, Fla., Academic Press). Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains. Additional classes include IgD, IgE, IgA, IgM and related proteins.

Methods for the generation and selection of monoclonal antibodies are well known in the art, as summarized for example in reviews such as Tramontano and Schloeder, Methods in Enzymology 178, 551-568, 1989. A recombinant KIF18A polypeptide (or fragment thereof) of the present invention may be used to generate antibodies in vitro. More preferably, the recombinant KIF18A of the present invention is used to elicit antibodies in vivo. In general, a suitable host animal is immunized with the recombinant KIF18A of the present invention. Advantageously, the animal host used is a mouse of an inbred strain. Animals are typically immunized with a mixture comprising a solution of the recombinant KIF18A of the present invention in a physiologically acceptable vehicle, and any suitable adjuvant, which achieves an enhanced immune response to the immunogen. By way of example, the primary immunization conveniently may be accomplished with a mixture of a solution of the recombinant KIF18A of the present invention and Freund's complete adjuvant, the mixture being prepared in the form of a water in oil emulsion. Typically the immunization will be administered to the animals intramuscularly, intradermally, subcutaneously, intraperitoneally, into the footpads, or by any appropriate route of administration. The immunization schedule of the immunogen may be adapted as required, but customarily involves several subsequent or secondary immunizations using a milder adjuvant such as Freund's incomplete adjuvant. Antibody titers and specificity of binding to the KIF18A can be determined during the immunization schedule by any convenient method including by way of example radioimmunoassay, or enzyme linked immunosorbant assay, which is known as the ELISA assay. When suitable antibody titers are achieved, antibody-producing lymphocytes from the immunized animals are obtained, and these are cultured, selected and cloned, as is known in the art. Typically, lymphocytes may be obtained in large numbers from the spleens of immunized animals, but they may also be retrieved from the circulation, the lymph nodes or other lymphoid organs. Lymphocytes are then fused with any suitable myeloma cell line, to yield hybridomas, as is well known in the art. Alternatively, lymphocytes may also be stimulated to grow in culture, and may be immortalized by methods known in the art including the exposure of these lymphocytes to a virus, a chemical or a nucleic acid such as an oncogene, according to established protocols. After fusion, the hybridomas are cultured under suitable culture conditions, for example in multi-well plates, and the culture supernatants are screened to identify cultures containing antibodies that recognize the hapten of choice. Hybridomas that secrete antibodies that recognize the recombinant KIF18A of the present invention are cloned by limiting dilution and expanded, under appropriate culture conditions. Monoclonal antibodies are purified and characterized in terms of immunoglobulin type and binding affinity.

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted F(ab')₂. This fragment can be further cleaved using a thiol reducing agent, and optionally a blocking group for the sulfhydryl groups resulting from cleavage of disulfide linkages, to produce 3.5 S Fab' monovalent fragments. Alternatively, an enzymatic cleavage using pepsin produces two monovalent Fab' fragments and an Fc fragment directly. These methods are described, for example, by Goldenberg, in U.S. Pat. Nos. 4,036,945 and 4,331,647, and references contained therein, which patents are hereby incorporated by reference in their entirety (see also Porter, R. R., Biochem. J., 73: 119-126, 1959). Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al. (Proc. Nat'l Acad. Sci. USA 69:2659-62, 1972). Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as $E.$ $coli.$ The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, all of which are hereby incorporated, by reference, in entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick and Fry Methods, 2: 106-10, 1991).

Humanized forms of non-human (e.g., murine) antibodies are chimeric molecules of immunoglobulins, immunoglobulin chains or fragments thereof (such as Fv, Fab, Fab', F(ab')₂ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues, which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321: 522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source, which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human monoclonal antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

As mentioned, the polynucleotides of the present invention are expressed in mesenchymal stem cells. Thus, the polynucleotides and polypeptides of the present invention may be used to differentiate between hematopoietic stem cells and mesenchymal stem cells and therefore be used as mesenchymal stem cell markers.

Thus, according to yet another aspect of the present invention there is provided a method of identifying a mesenchymal stem cell comprising identifying in a biological sample a cell expressing the polynucleotides or polypeptides of the present invention.

As used herein the phrase "biological sample" refers to a cellular sample of tissue or fluid isolated from an individual which comprises bone marrow cells, including, but not limited to, for example, bone marrow, plasma, serum, spinal fluid, lymph fluid, the external sections of the skin, respiratory, intestinal, and genitourinary tracts, tears, saliva, milk, blood cells, synovial cell fluid, tumors, organs such as synovial tissue and also samples of in vivo cell culture constituents, cell-lines and cultured cells. Preferably, the biological sample is a bone marrow sample. Bone marrow is typically aspirated surgically using methods known in the art.

Identification of cells according to this aspect of the present invention may be effected at the polynucleotide levels using methods which are well known in the art. For example, oligonucleotides can be used which are capable of binding to sequences which are specific to mesenchymal stem cell KIF18A polynucleotides and not to other KIF18A variants such as variant A (SEQ ID NO:11) as described in Table 1 of the Examples section which follows. Such sequences may be present in the untranslated region or the open reading frame of the isolated polynucleotides.

As used herein, the term "oligonucleotide" refers to a single-stranded or double-stranded oligomer or polymer of ribonucleic acid (RNA) or deoxyribonucleic acid (DNA) or mimetics thereof. This term includes oligonucleotides composed of naturally occurring bases, sugars, and covalent internucleoside linkages (e.g., backbone), as well as oligonucleotides having non-naturally occurring portions, which function similarly to respective naturally occurring portions.

As used herein, the phrase "capable of hybridizing" refers to forming a double strand molecule such as RNA:RNA, RNA:DNA and/or DNA:DNA molecules.

Oligonucleotides designed according to the teachings of the present invention can be generated according to any oligonucleotide synthesis method known in the art, such as enzymatic synthesis or solid-phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Md.; Perbal, B. (1988), "A Practical Guide to Molecular Cloning," John Wiley & Sons, New York; and Gait, M. J., ed. (1984), "Oligonucleotide Synthesis"; utilizing solid-phase chemistry, e.g. cyanoethyl phosphoramidite followed by deprotection, desalting, and purification by, for example, an automated trityl-on method or HPLC.

The oligonucleotide of the present invention is of at least 17, at least 18, at least 19, at least 20, at least 22, at least 25, at least 30 or at least 40, bases specifically hybridizable with polynucleotide sequences of the present invention.

The oligonucleotides of the present invention may be used in a variety of methods known in the art for detecting MS-KIF18A polynucleotides thereby identifying mesenchymal stem cells. Examples of such methods are summarized below.

Northern Blot analysis: This method involves the detection of a particular RNA in a mixture of RNAs. An RNA sample is denatured by treatment with an agent (e.g., formaldehyde) that prevents hydrogen bonding between base pairs, ensuring that all the RNA molecules have an unfolded, linear conformation. The individual RNA molecules are then separated according to size by gel electrophoresis and transferred to a nitrocellulose or a nylon-based membrane to which the denatured RNAs adhere. The membrane is then exposed to labeled DNA probes. Probes may be labeled using radio-isotopes or enzyme linked nucleotides. Detection may be using autoradiography, calorimetric reaction or chemiluminescence. This method allows both quantitation of an amount of particular RNA molecules and determination of its identity by a relative position on the membrane which is indicative of a migration distance in the gel during electrophoresis.

RT-PCR analysis: This method uses PCR amplification of relatively rare RNAs molecules. First, RNA molecules are purified from the cells and converted into complementary DNA (cDNA) using a reverse transcriptase enzyme (such as an MMLV-RT) and primers such as, oligo dT, random hexamers or gene specific primers. Then by applying gene specific primers and Taq DNA polymerase, a PCR amplification reaction is carried out in a PCR machine. Those of skills in the art are capable of selecting the length and sequence of the gene specific primers and the PCR conditions (i.e., annealing temperatures, number of cycles and the like) which are suitable for detecting specific RNA molecules. It will be appreciated that a semi-quantitative RT-PCR reaction can be employed by adjusting the number of PCR cycles and comparing the amplification product to known controls.

RNA in situ hybridization stain: In this method DNA or RNA probes are attached to the RNA molecules present in the cells. Generally, the cells are first fixed to microscopic slides to preserve the cellular structure and to prevent the RNA molecules from being degraded and then are subjected to hybridization buffer containing the labeled probe. The hybridization buffer includes reagents such as formamide and salts (e.g., sodium chloride and sodium citrate) which enable specific hybridization of the DNA or RNA probes with their target mRNA molecules in situ while avoiding non-specific binding of probe. Those of skills in the art are capable of adjusting the hybridization conditions (i.e., temperature, concentration of salts and formamide and the like) to specific probes and types of cells. Following hybridization, any unbound probe is washed off and the slide is subjected to either a photographic emulsion which reveals signals generated using radio-labeled probes or to a colorimetric reaction which reveals signals generated using enzyme-linked labeled probes.

In situ RT-PCR stain: This method is described in Nuovo G J, et al. [Intracellular localization of polymerase chain reaction (PCR)-amplified hepatitis C cDNA. Am J Surg Pathol. 1993, 17: 683-90] and Komminoth P, et al. [Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract. 1994, 190: 1017-25]. Briefly, the RT-PCR reaction is performed on fixed cells by incorporating labeled nucleotides to the PCR reaction. The reaction is carried on using a specific in situ RT-PCR apparatus such as the laser-capture microdissection PixCell I LCM system available from Arcturus Engineering (Mountainview, Calif.).

Oligonucleotide microarray—In this method oligonucleotide probes capable of specifically hybridizing with the polynucleotides of the present invention are attached to a solid surface (e.g., a glass wafer). Each oligonucleotide probe is of approximately 20-25 nucleic acids in length. To detect the expression pattern of the polynucleotides of the present invention in a specific cell sample (e.g., blood cells), RNA is extracted from the cell sample using methods known in the art (using e.g., a TRIZOL solution, Gibco BRL, USA). Hybridization can take place using either labeled oligonucleotide probes (e.g., 5'-biotinylated probes) or labeled fragments of complementary DNA (cDNA) or RNA (cRNA). Briefly, double stranded cDNA is prepared from the RNA using reverse transcriptase (RT) (e.g., Superscript II RT), DNA ligase and DNA polymerase I, all according to manufacturer's instructions (Invitrogen Life Technologies, Frederick, Md., USA). To prepare labeled cRNA, the double stranded cDNA is subjected to an in vitro transcription reaction in the presence of biotinylated nucleotides using e.g., the BioArray High Yield RNA Transcript Labeling Kit (Enzo, Diagnostics, Affymetix Santa Clara Calif.). For efficient hybridization the labeled cRNA can be fragmented by incubating the RNA in 40 mM Tris Acetate (pH 8.1), 100 mM potassium acetate and 30 mM magnesium acetate for 35 minutes at 94° C. Following hybridization, the microarray is washed and the hybridization signal is scanned using a confocal laser fluorescence scanner which measures fluorescence intensity emitted by the labeled cRNA bound to the probe arrays.

For example, in the Affymetrix microarray (Affymetrix®, Santa Clara, Calif.) each gene on the array is represented by a series of different oligonucleotide probes, of which, each probe pair consists of a perfect match oligonucleotide and a mismatch oligonucleotide. While the perfect match probe has a sequence exactly complimentary to the particular gene, thus enabling the measurement of the level of expression of the particular gene, the mismatch probe differs from the perfect match probe by a single base substitution at the center base position. The hybridization signal is scanned using the Agilent scanner, and the Microarray Suite software subtracts the non-specific signal resulting from the mismatch probe from the signal resulting from the perfect match probe.

Alternatively or additionally and as mentioned hereinabove, mesenchymal stem cells may be identified by detecting the polypeptides of the present invention. Following is a non-limiting list of methods which be used to identify mesenchymal stem cells by detecting the polypeptides of the present invention.

Western blot: This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, calorimetric reaction or chemiluminescence. This method allows both quantitation of an amount of substrate and determination of its identity by a relative position on the membrane which is indicative of a migration distance in the acrylamide gel during electrophoresis.

Radio-immunoassay (RIA): In one version, this method involves precipitation of the desired protein (i.e., the substrate) with a specific antibody and radiolabeled antibody binding protein (e.g., protein A labeled with $I^{125}$) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Fluorescence activated cell sorting (FACS): This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Immunohistochemical analysis: This method involves detection of a substrate in situ in fixed cells by substrate specific antibodies. The substrate specific antibodies may be enzyme linked or linked to fluorophores. Detection is by microscopy and subjective or automatic evaluation. If enzyme linked antibodies are employed, a calorimetric reaction may be required. It will be appreciated that immunohistochemistry is often followed by counterstaining of the cell nuclei using for example Hematoxyline or Giemsa stain.

In situ activity assay: According to this method, a chromogenic substrate is applied on the cells containing an active enzyme and the enzyme catalyzes a reaction in which the substrate is decomposed to produce a chromogenic product visible by a light or a fluorescent microscope.

In vitro activity assays: In these methods the activity of a particular enzyme is measured in a protein mixture extracted from the cells. The activity can be measured in a spectrophotometer well using calorimetric methods or can be measured in a non-denaturing acrylamide gel (i.e., activity gel). Following electrophoresis the gel is soaked in a solution containing a substrate and calorimetric reagents. The resulting stained band corresponds to the enzymatic activity of the protein of interest. If well calibrated and within the linear range of response, the amount of enzyme present in the sample is proportional to the amount of color produced. An enzyme standard is generally employed to improve quantitative accuracy.

As mentioned herein above, the present inventor has shown that MS-KIF18A binds to estrogen receptors (FIGS. 14A-B, 15). Specifically, the present inventor has shown using bioinformatic techniques that MS-KIF18A comprises in its cargo domain a region homologous to the boundary region between the hinge and ligand-binding domains (LBD) of ERα (28.6% of identity) and at the coiled coil region of MS-KIF18A, a region homologous to the C-terminal of ERα-LBD (31% identity)—see FIG. 12. Since MS-KIF18A is observed in the cell nucleus, dispersed throughout the cell cytoplasm, and localized at the plasma ruffles (FIGS. 9-12) in a localization pattern similar to the estrogen receptor itself, the present inventor has postulated that the polynucleotides and/or polypeptides of the present invention may be used to shuttle the estrogen receptor from the cell cytoplasm to the nucleus and therefore may be used to modulate estrogen signaling.

Thus, according to yet another aspect of the present invention there is provided a method of modulating estrogen signaling in a cell. The method is affected by contacting the cell with an agent capable of regulating an expression and/or activity of the polypeptide of the present invention (e.g., SEQ ID NO: 2), thereby modulating estrogen signaling in the cell.

As used herein, the phrase "estrogen signaling" refers to the biochemical signaling (e.g., activation of mitogen activated protein kinases) which result from binding of estrogen to its receptor and/or the resulting biological physiological outcome (e.g., maintenance of bone density). Accordingly, the phrase "estrogen signaling" may incorporate such functions as estrogen receptor shuttling from the cytoplasm to the nucleus and any further down-stream actions of estrogen.

According to this aspect of the present invention, the contacting may be effected both in vivo and/or ex vivo.

As mentioned, the method of this aspect of the present invention is affected by contacting cells with an agent capable of regulating KIF18A polypeptides.

The term "regulating" as used herein refers to upregulating (i.e., increasing) or downregulating (i.e., decreasing) activity and or expression of the polypeptides of the present invention.

It will be appreciated that modulating estrogen signaling may be effected by regulating one particular isoform of KIF18A or any combination of isoforms of KIF18A. Accordingly, the agents of the present invention may be directed against a unique sequence present in a KIF18A isoform or polynucleotide encoding same or may be directed against a sequence common to a group of KIF18A isoforms or polynucleotides encoding same.

Agents capable of upregulating the polypeptides of the present invention may comprise the isolated polynucleotides of the present invention.

Such polynucleotide sequences are typically inserted into expression vectors to enable expression of the recombinant polypeptide. The expression vector of the present invention includes additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals).

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Examples of mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Recombinant viral vectors may also be used to synthesize the polynucleotides of the present invention. Viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Bone marrow cells can be targeted using the human T cell leukemia virus type I (HTLV-I).

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of the present invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Down-regulating the function of KIF18A can be effected at the RNA level or at the protein level. It will be appreciated that down-regulating the function of KIF18A can only be effected in cells where KIF18A is expressed. Thus, for example, down-regulating the function of MS-KIF18A can be effected in testes cells and mesenchymal stem cells.

According to one embodiment of this aspect of the present invention the agent is an oligonucleotide capable of specifically hybridizing (e.g., in cells under physiological conditions) to a polynucleotide comprising a nucleic acid sequence encoding a KIF18A polypeptide. Such oligonucleotides have been described hereinabove.

The prior art teaches of a number of delivery strategies which can be used to efficiently deliver oligonucleotides into a wide variety of cell types [see, for example, Luft J Mol Med 76: 75-6 (1998); Kronenwett et al., Blood 91: 852-62 (1998); Rajur et al., Bioconjug Chem 8: 935-40 (1997); Lavigne et al., Biochem Biophys Res Commun 237: 566-71 (1997) and Aoki et al., (1997) Biochem Biophys Res Commun 231: 540-5 (1997)].

A small interfering RNA (siRNA) molecule is another example of an agent capable of downregulating the expression of a KIF18A. RNA interference is a two-step process. During the first step, which is termed the initiation step, input dsRNA is digested into 21-23 nucleotide (nt) small interfering RNAs (siRNA), probably by the action of Dicer, a member of the RNase III family of dsRNA-specific ribonucleases, which cleaves dsRNA (introduced directly or via an expressing vector, cassette or virus) in an ATP-dependent manner. Successive cleavage events degrade the RNA to 19-21 bp duplexes (siRNA), each strand with 2-nucleotide 3' overhangs [Hutvagner and Zamore Curr. Opin. Genetics and Development 12:225-232 (2002); and Bernstein Nature 409: 363-366 (2001)].

In the effector step, the siRNA duplexes bind to a nuclease complex to form the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr. Opin. Genetics and Development 12:225-232 (2002); Hammond et al., (2001) Nat. Rev. Gen. 2:110-119 (2001); and Sharp Genes. Dev. 15:485-90 (2001)]. Although the mechanism of cleavage is still to be elucidated, research indicates that each RISC contains a single siRNA and an RNase [Hutvagner and Zamore Curr. Opin. Genetics and Development 12:225-232 (2002)].

Because of the remarkable potency of RNAi, an amplification step within the RNAi pathway has been suggested. Amplification could occur by copying of the input dsRNAs, which would generate more siRNAs, or by replication of the siRNAs formed. Alternatively or additionally, amplification could be effected by multiple turnover events of the RISC [Hammond et al., Nat. Rev. Gen. 2:110-119 (2001), Sharp Genes. Dev. 15:485-90 (2001); Hutvagner and Zamore Curr. Opin. Genetics and Development 12:225-232 (2002)]. For more information on RNAi see the following reviews Tuschl ChemBiochem. 2:239-245 (2001); Cullen Nat. Immunol. 3:597-599 (2002); and Brantl Biochem. Biophys. Act. 1575: 15-25 (2002).

Synthesis of RNAi molecules suitable for use with the present invention can be effected as follows. First, the KIF18A polynucleotide sequence target is scanned downstream for AA dinucleotide sequences. Occurrence of each AA and the 3' adjacent 19 nucleotides is recorded as potential siRNA target sites.

Second, potential target sites are compared to an appropriate genomic database (e.g., human, mouse, rat etc.) using any sequence alignment software, such as the BLAST software available from the NCBI server wwwdotncbidotnlmdotnih-dotgov/Blast/). Putative target sites that exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

Another agent capable of downregulating the expression of a KIF18A polypeptide is a DNAzyme molecule capable of specifically cleaving its encoding polynucleotide. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl. Acad. Sci. USA 1997; 94:4262). A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine: pyrimidine junctions (Santoro, S. W. & Joyce, G. F. Proc. Natl. Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al., 2002, Abstract 409, Ann Meeting Am Soc Gen Ther wwwdotasgtdotorg). In another application, DNAzymes complementary to bcr-abl oncogenes were successful in inhibiting the oncogenes expression in leukemia cells, and lessening relapse rates in autologous bone marrow transplant in cases of Chronic Myelogenous Leukemia (CML) and Acute Lymphocytic Leukemia (ALL).

Another agent capable of downregulating the expression of a KIF18A is a ribozyme molecule capable of specifically cleaving its encoding polynucleotide. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications.

An additional method of downregulating the function of the KIF18A of the present invention is via triplex forming oligonucleotides (TFOs). In the last decade, studies have shown that TFOs can be designed which can recognize and bind to polypurine/polypirimidine regions in double-stranded helical DNA in a sequence-specific manner. Thus the DNA sequence encoding the polypeptide of the present invention can be targeted thereby down-regulating the polypeptide.

The recognition rules governing TFOs are outlined by Maher III, L. J., et al., Science (1989) 245:725-730; Moser, H. E., et al., Science (1987) 238:645-630; Beal, P. A., et al., Science (1991) 251:1360-1363; Cooney, M., et al., Science (1988) 241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer (2003) J Clin Invest; 112:487-94).

In general, the triplex-forming oligonucleotide has the sequence correspondence:

| oligo | 3'--A | G | G | T |
|-------|-------|---|---|---|
| duplex | 5'--A | G | C | T |
| duplex | 3'--T | C | G | A |

However, it has been shown that the A-AT and G-GC triplets have the greatest triple helical stability (Reither and Jeltsch (2002), BMC Biochem, Sept12, Epub). The same authors have demonstrated that TFOs designed according to the A-AT and G-GC rule do not form non-specific triplexes, indicating that the triplex formation is indeed sequence specific.

Thus for any given sequence in the regulatory region a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and subsequent formation of the triple helical structure with the target DNA, induces steric and functional changes, blocking transcription initiation and elongation, allowing the introduction of desired sequence changes in the endogenous DNA and results in the specific downregulation of gene expression. Examples of such suppression of gene expression in cells treated with TFOs include knockout of episomal supFG1 and endogenous HPRT genes in mammalian cells (Vasquez et al., Nucl Acids Res. (1999) 27:1176-81, and Puri, et al., J Biol Chem, (2001) 276:28991-98), and the sequence- and target-specific downregulation of expression of the Ets2 transcription factor, important in prostate cancer etiology (Carbone, et al., Nucl Acid Res. (2003) 31:833-43), and the pro-inflammatory ICAM-1 gene (Besch et al., J Biol Chem, (2002) 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res (2000); 28:2369-74).

Additionally, TFOs designed according to the abovementioned principles can induce directed mutagenesis capable of effecting DNA repair, thus providing both downregulation and upregulation of expression of endogenous genes [Seidman and Glazer, J Clin Invest (2003) 112:487-94]. Detailed description of the design, synthesis and administration of effective TFOs can be found in U.S. Patent Application Nos. 2003 017068 and 2003 0096980 to Froehler et al., and 2002 0128218 and 2002 0123476 to Emanuele et al., and U.S. Pat. No. 5,721,138 to Lawn.

As mentioned hereinabove, down-regulating the function of a KIF18A polypeptide can also be affected at the protein level.

Thus, another example of an agent capable of downregulating a polypeptide of the present invention is an antibody or antibody fragment capable of specifically binding a KIF18A polypeptide or a particular isoform thereof, preferably to its active site, thereby preventing its function. Methods of producing such antibodies are described hereinabove.

Regardless of the agents employed the effect of same on cells may be determined using well known molecular biology, biochemical or cell biology techniques. The specific assay will be selected according to the particular researcher's needs and expertise.

It will be appreciated that up-regulating the function of a KIF18A polypeptide will typically result in an enhanced estrogen effect since more estrogen will reach the nucleus and thereby have an effect. It is known that in the male testis, disruption of ERα, either by knockout (ERαKO) or by treatment with a pure antiestrogen, results in dilution of cauda epididymal sperm, disruption of sperm morphology, inhibition of sodium transport and subsequent water reabsorption, increased secretion of $Cl^-$, and eventual decreased fertility [Hess et al., Anim. Reprod., v.1.n.1, p. 5-30, October/December 2004].

Therefore, according to another aspect of the present invention, there is provided a method of treating infertility, the method comprising administering to a subject in need thereof a therapeutically effective amount a KIF18A polypeptide thereby treating infertility.

As used herein, the phrase "KIF18A polypeptide" refers to any expression product of the KIF18A gene including, but not limited to MS-KIF18A and all the variants listed in Table 1 in the Examples section hereinbelow.

According to this aspect of the present invention, the phrase "infertility" refers to the inability or diminished ability to produce offspring.

It has also been shown that estrogen modulates osteogenic activity, and apoptosis in mesenchymal stem cells of osteoporotic mice [Zhou S. et al. Journal of Cellular Biochemistry 2001 81 144-155]. Therefore modulating MS-KIF18A in mesenchymal stem cells either in vivo or ex vivo may affect the ability of mesenchymal cell to differentiate into bone tissue.

The above described agent of the present invention can be provided to the individual per se, or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the polypeptide or antibody preparation, which is accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer the preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Cloning and Analysis of MS-KIF18A

In order to identify polypeptides of interest, an antibody raised against a marrow stromal osteogenic cell line (MBA-15) was used to immunoclone polypeptides from a human stromal cell expression library.

Materials and Methods

Cloning of MS-KIF18A gene: An expression library of human stromal cells (Stratagene, La Jolla, Calif.) was plated on LB-ampicillin agar plates and induced with isopropyl D-1-thiogalactopyranoside (IPTG, Sigma, USA) for secretion of fusion protein that was subsequently captured onto nitrocellulose. For cloning, the monoclonal antibody, MMS-85 (Benayahu et al, 1995, J Bone Miner Res 10, 1496-503) was reacted with the proteins captured on the nitrocellulose. The colonies that were the most highly expressed were selected and subjected to sequencing with universal T3, T7 primers or cDNA specific primers in two directions on double-stranded BS plasmid (Automatic sequencer Applied Bio-systems, Tel Aviv University, Israel).

Expressing the MS-KIF18A gene: The full-length MS-KIF18A cDNA was amplified using 5' primer containing a BamHI restriction site (CGGGATCCTCAACAATGTCT-GTCACTGAG) SEQ ID NO:4 and a 3' primer containing an XhoI restriction site (CCGCTCGAGGATCAACT-TCATTTTGCTT GG) SEQ ID NO:5. The insert was digested with both restriction enzymes and sub-cloned into pcDNA3.1-His-C expression plasmid (Invitrogen, USA). The pcDNA3.1-His-C-MS-KIF18A vector was confirmed by sequencing.

Bioinformatic analysis: MS-KIF18A cDNA and its genomic structure were analyzed using various bioinformatic tools available at sapiensdotwustldotedu/-zkanTAP, www-dotncbidotnlmdotnihdotgov/BLAST. Protein structure, open reading frame, sub cellular localization and functional domains were obtained at wwwdotexpasydotchcotCootdot-embl-heidelbergdotde/SMART, wwwdotchdotembnetdot-org/software/COIL_formdothtml, elmdoteudotorg, www-dotabgentdotcom/sumoplatdothtml. Phosphorylation modification was analyzed wwwdotcbsdotdtudotdk/services/NetPhos. The multiple alignment tools were obtained at wwwdotebidotacdotuk/clustalw/.

In vitro culture: Ex-vivo primary cultured human mesenchymal stem cells (MSC) from surgical aspirates of bone marrow were cultured as previously described [Shur et al, 2002, J Cell. Biochem. 87, 51-57]. Cells were plated at low-density ($1.5 \times 10^4$ cells/cm$^2$) and were cultured in growth medium containing Dulbecco's modified essential Medium (DMEM) (Gibco, USA) with the addition of 10% heat-inactivated fetal calf serum (FCS, Gibco, USA) supplemented with 1% glutamine and 1% Penicillin/Streptomycin at 37° C. in a humidified atmosphere of 10% $CO_2$ in air. MBA-15, a pre-osteogenic marrow stromal cell line derived from primary cultures of adherent layers of bone marrow (Benayahu et al., 1989, J Cell Physiol. 140, 1-7) were cultured in growth medium in a humidified atmosphere of 5% $CO_2$ at 37° C. Monkey kidney embryonic cell line COS-7 cells were grown in DMEM supplemented with 5% FCS, 1% glutamine and 1% Penicillin/Streptomycin in a humidified atmosphere of 5% $CO_2$ at 37° C.

COS-7 cells were transiently transfected with the expression construct pcDNA3.1-His-C— MS-KIF18A using PolyFect reagent (Quiagen, USA) according to the manufacture's protocol. For transfection, $5 \times 10^5$ cells were plated on 60 mm culture plates (Nunc, Denmark). Following 24 hours, the cells were rinsed twice with PBS and fresh medium was added with 2.5 µg DNA. Following 16 hours, the cells were harvested for subsequent immunoprecipitation (IP) and Western blot (WB) analysis.

Gene expression analysis: Total RNA was extracted from MSC using EZ RNA (Biological industries, Bet-Haemek, Israel) and analyzed by Northern blot and RT-PCR. For Northern blot, RNA was separated on a formaldehyde gel, blotted on to a nylon membrane (Bio Rad, USA) and probed with radio labeled [$^{32}$P]-CTP cDNA with random prime (Stratagen, USA). (SEQ ID NO: 1) Following an overnight hybridization at 65° C., the membrane was exposed to X-OMAT AR film (Kodak, USA).

For RT-PCR, cDNA was prepared using avian myeloblastosis virus reverse transcriptase (AMV-RT) and oligo-dT (Takara Shuzo Co. Ltd., Japan). MS-KIF18A expression was analyzed by PCR with super term DNA polymerase using specific primers; F-TGTAAAGATCTGTAATGAGCAGAAG (SEQ ID NO:6) and R-CCAAGTCCTCCTGTCCACAT (SEQ ID NO: 7) with expected size 1180 bp, and F-GCTTGGGTTTGAATATTGTG (SEQ ID NO: 8), R-TTGCAAGTCTATGATCT CGTTT (SEQ ID NO: 9) with expected size 1600 bp. The integrity of the RNA and the efficiency of the RT reaction were verified by amplification of transcript of Glucose-3-Phosphate Dehydrogenase (G3PDH). The cDNA was amplified using a PCR machine (MJ, USA) at 94° C. for 1 minute, followed by touchdown annealing from 69° C. to 55° C. and extension at 72° C. for 1 minute. Amplification proceeded with 24 cycles of annealing at 55° C. for 45 seconds and extension at 72° C. for 1 minute. G3PDH was amplified for 22 cycles with annealing at 58° C. for 45 seconds, and extension at 72° C. for 1 minute with a final extension of 7 minutes at 72° C. for both reactions. PCR products were analyzed by electrophoresis on a 1% agarose gel (SeaKem GTG, FMC, USA) in Tris-Borate-EDTA (TBE) buffer, stained with ethidium bromide and visualized under UV light.

Antibody generation: An antibody to MS-KIF18A was generated which was raised against the synthetic peptide TNQNVIKKQNKDLK (SEQ ID NO: 10), that was KLH conjugated and used for immunization of rabbits. The rabbit serum was IgG purified on G-protein column (Pharmacia, USA).

Western blot analysis and Immunoprecipitation: Cells were harvested from cultures, washed twice with ice-cold PBS and collected in presence of protease inhibitors (Phenylmethylsulfonyl fluoride PMSF, 1 mM; 1-Chloro-3-tosylamido-4-phenyl-2-butanone, TPCK, 10 µg/ml; Aprotinin, 10 µg/ml (Sigma, USA) and phosphatase inhibitor cocktails I and II (Sigma, USA). Samples were spun down at 1500 rpm for 4 minutes and pellets were reconstituted in lyses buffer (50 mM Tris pH 7.5, 150 mM NaCl, 1% NP-40, and protease and phosphatase inhibitors, as above). Following a 20 minute incubation at 4° C., samples were centrifuged at 16,000 g for 5 minutes.

For immunoprecipitation (IP), anti-MS-KIF18A and protein-A sepharose beads (Sigma, USA) were added to lysates and samples were incubated overnight at 4° C. Immunocomplexes were precipitated at 16,000 g for 1 minute and washed 4 times with lyses buffer. The washed beads were re-suspended in Lamelli sample buffer and boiled for 3 minutes. The proteins were separated on 8% SDS-PAGE gel for 2 hours and transferred to nitrocellulose for 1.5 hours.

For Western blot, the membranes were blocked with 5% BSA in TBST (50 mM Tris, pH-7.5, 150 mM NaCl, 0.1% Tween-20, Sigma, USA) for 1 hour at RT or overnight and than incubated with anti-MS-KIF18A. The membranes were washed with TBST and incubated with goat anti-rabbit or goat anti-mouse conjugated to biotin (Dako, Denmark) for 40 minutes at RT and Extravidin-Peroxidase (Sigma, USA) for detection with chemiluminescent substrate (Pierce, USA).

Confocal Immunofluorescence microscopy: MBA-15 cells were grown on cover slips, fixed in 4% paraformaldehyde in phosphate buffered saline (PBS) for 20 minutes at room temperature (RT), washed with PBS and permeabilized with 0.1% Triton in PBS for 5 minutes on ice. Following a wash with PBS, the cells were reacted with primary antibodies as indicated. The cells was incubated for 1 hour at RT with the primary antibody, washed with PBS and stained with an appropriate secondary antibody for 1 hour at RT. Slides were washed with PBS and mounted using ProLong anti-fade mounting media (Molecular Probes, USA).

Primary antibodies included polyclonal anti-MS-KIF18A and monoclonal anti-tubulin (Sigma, Israel). Secondary antibodies were conjugated to fluorescein isothiocyanate (FITC, Jackson Immunoresearch Laboratories, USA) or Texas-Red or Rhodamine (Sigma, USA). Actin filaments were stained with phalloidine (Sigma, USA). Cell nuclei were stained with 4',6'-diamidino-2-phenylindole hydrochloride (DAPI, Molecular probes, USA). Images were acquired on Leica Microsystems (Deerfield, Ill., USA) or Zeiss 410 laser scanning confocal microscopes.

Results

Figure 1:
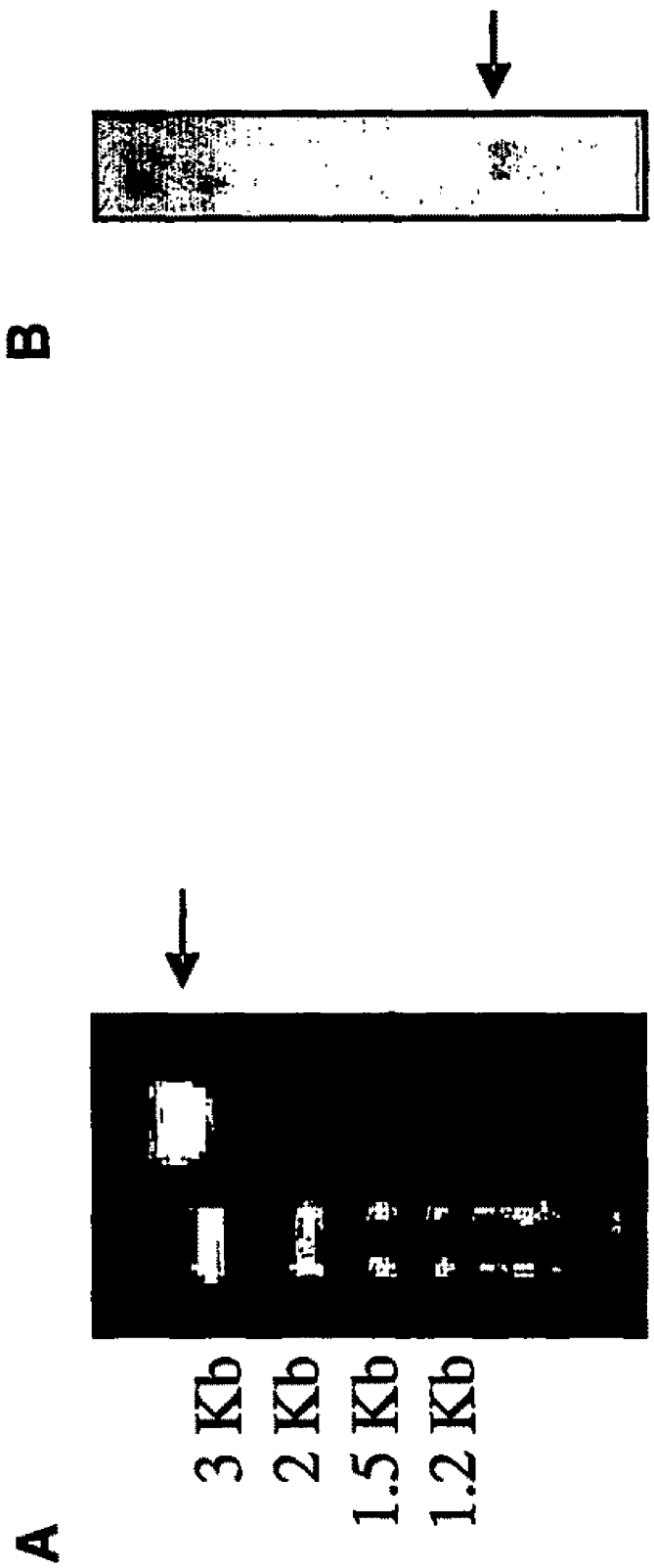
FIGS. 1A-B are photographs depicting the size and expression of MS-KIF18A in mesenchymal stem cells.
Figure 2:
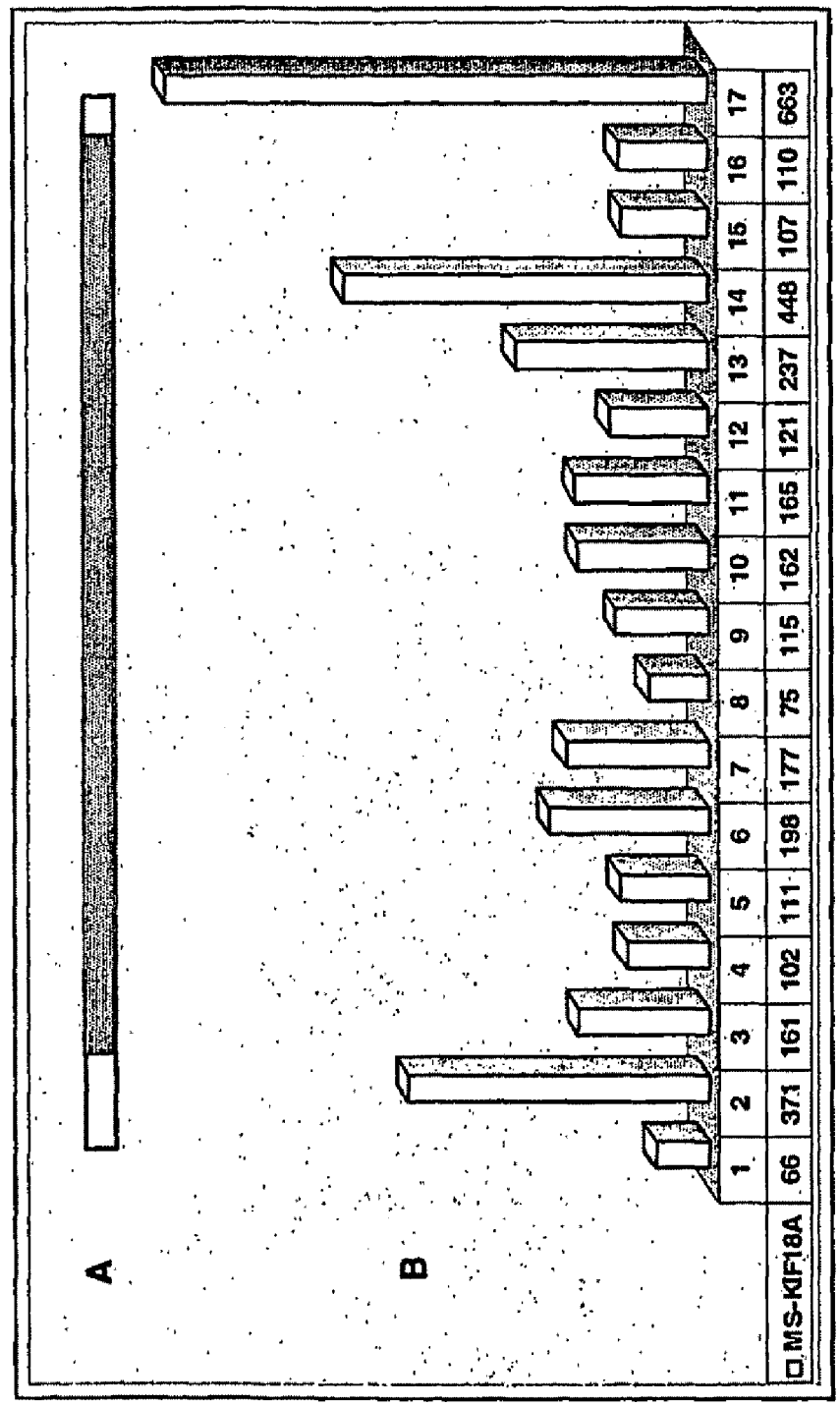
FIGS. 2A-B are schematic illustrations of the structure of the cDNA encoding MS-KIF18A.

Cloning of MS-KIP18A: Three full-length cDNAs were cloned and confirmed by Southern blot (data not shown) and enzymatic restriction. PCR amplification of the full length cDNA resulted in a 3407 bp transcript—SEQ ID NO: 1 (FIG. 1A). A single transcript was detected by Northern blot analysis in RNA harvested from MSCs (FIG. 1B). Blast analysis of the cloned cDNA related it to the KIF18A gene. The KIF18A gene is mapped to human chromosome 11p14 and spans approximately 87.57 kb. Since it was shown to be expressed in mesenchymal stem cells, the novel cDNA was named MS-KIF18A. The MS-KIF18A cDNA contains 17 exons varying in size from 66 bp to 663 bp (FIG. 2B). Homologous transcripts from KIF18A were identified by Blast. These transcripts are expressed in testis and trachea tissues (Table 1). The various transcripts differ in their UTR and ORF composition (Table 1).

TABLE 1

| Accession No. | cDNA, bp | origin | 5'UTR | ORF | First M | Protein length | 3'UTR |
|---|---|---|---|---|---|---|---|
| MS-KIF18A (SEQ ID NO: 1) | 3407 | MSC | 113 | +2 | 113 | 898 | 581 |
| MS-KIF18Ab (SEQ ID NO: 3) | 3451 | MSC | 157 | +1 | 157 | 898 | |
| A: NM 031217 | 3379 | testis, colon | 84 | +3 | 84 | 898 (A/G, P/S, V/I) | 581 |
| B: AL136819 | 3032 | testis | 130 | +1 | 130 | 898 (V/I) | 206 |
| C: BC026090 | 2168 | testis | 163 | +1 | 163 | Frame shift | — |
| D: AK093850 | 2263 | trachea | — | +3 | 30 | 678 | 197 |
| E: BC048347 | 2942 | Testis, embryonic carcinoma | 48 | +3 | 48 | 898 | 198 |

Figure 3:
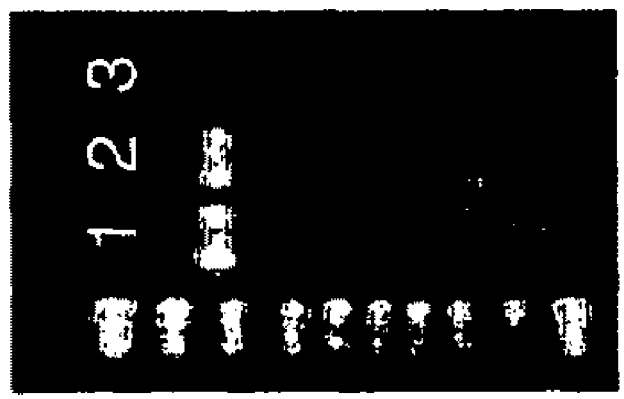
FIG. 3 is a photograph of an RT-PCR analysis confirming the presence of a second transcript of MS-KIF18A in mesenchymal stromal cells (SEQ ID NO: 3). Lanes 1 and 2—cDNA from two separate MSC donors, lane 3—DDW (negative control).

The longest 5' UTR of all the transcripts was 163 bp (Table 1, transcript C, gi BC026090). Transcript Assembly Program (TAP) predicted the untranslated first exon is 163 bp which is 50 bp longer than MS-KIF18A. To test whether such a transcript is expressed in MSC, RT-PCR analysis was performed using a 5' primer designed for the predicted 5' UTR (SEQ ID NO: 9) and an internal primer for MS-KIF18A cDNA (SEQ ID NO: 8). The expected 1600 bp PCR product was amplified from MSC (FIG. 3), thus confirming a longer transcript of 3451 bp with an extended 5' UTR similar to transcript C (gi BC026090) SEQ ID NO: 3. Multiple sequence alignment of the transcripts of the KIF18A gene revealed that transcripts B (gi AL136819), D (gi AK093850) and E (gi BC048347) (Table 1) contain shorter 3' UTR than the cloned MS-KIF18A, suggesting different regulation of KIF18A mRNA processing.

Figure 4:
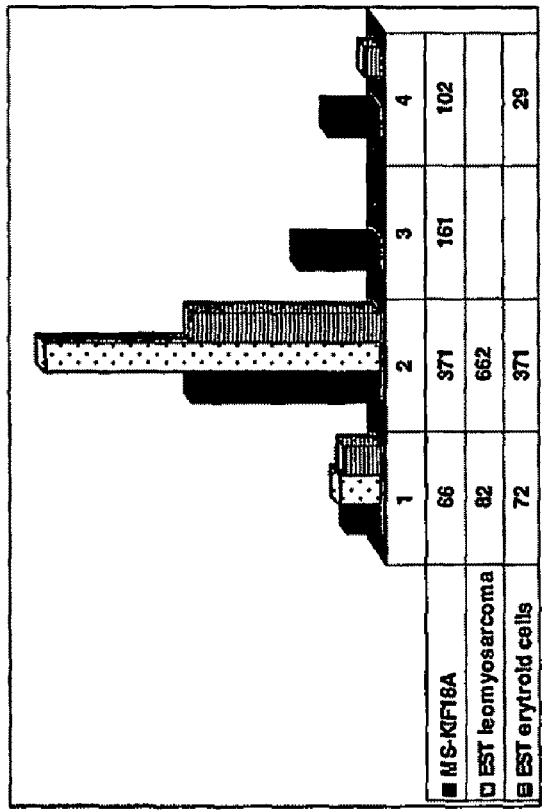
FIGS. 4A-B are graphs and schematic illustrations comparing MS-KIF18A (SEQ ID NO: 1) to EST from Erythroid tissue (BG944537) or Leomyosarcoma (BC035917).

Sequence alignment of the ORF of transcript A (NM 031217) and transcript B (AL136819), identified single-nucleotide polymorphisms (SNPs). These SNPs result in amino acid substitutions in the protein sequence. The protein encoded by transcript D (gi AK093850) lacks the N-terminal part and transcript C (giBC026090) has a frame shift which results in a truncated protein (Table 1). Two additional ESTs, identified from erythroid tissue BG944537 (478 bp) and Leomyosarcoma BC035917 (744 bp) represent alternative splice forms of KIF18A gene see FIGS. 4A-B. The EST from erythroid cells (gi BG944537) is composed of exons 1 and 2 and partial sequences of exon 4, skipping exon 3. The EST from leomyosarcoma tissue (gi BC035917) is composed of exons 1 and 2 and a partial sequence from the intron proceeding exon 2. The ORFs of these ESTs encode part of a kinesin motor domain with amino acid substitutions at the C-terminus of the protein. The amino acids encoded by this intron sequence are not encoded by the MS-KIF18A.

Figure 5:
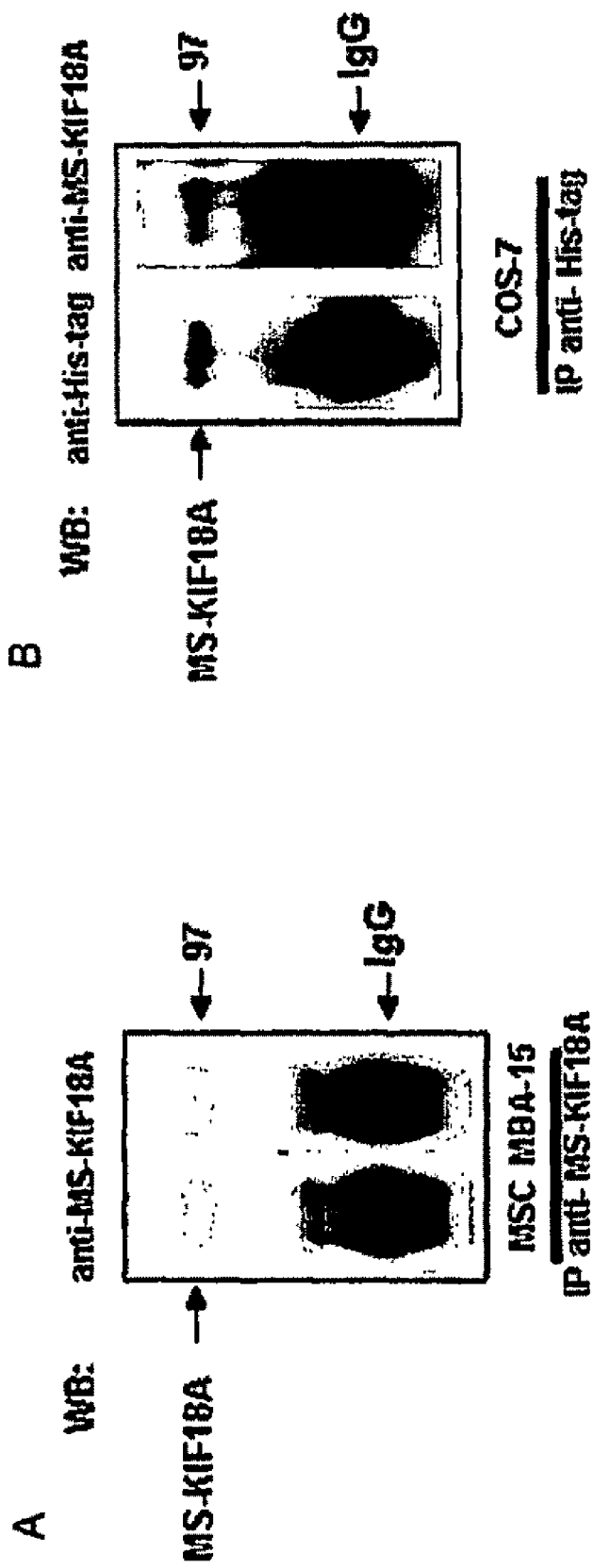
FIGS. 5A-B are Western blots identifying the presence of MS-KIF18A—SEQ ID NO:2.

Bioinformatic analysis of the MS-KIF18A protein: The largest open reading frame (ORF) of MS-KIF18A is 2697 bp (FIG. 2A), with the first in-frame methionine at 113 bp of exon 2 and the first stop codon appearing in the last exon at 2809 bp. This ORF encodes for a polypeptide of 898 amino acids, with an expected molecular weight of 102 kDa and pI 9.1. To study MS-KIF18A expression an antibody was developed to a synthetic peptide (see Material and Methods). This antibody was used in immunological studies on MBA-15 cells and primary cultured human MSCs. IP and WB analyses of these cells confirmed that the protein migrated at 100 kDa as expected from the bioinformatic predictions (FIG. 5A). Transfection of COS-7 cells with pcDNA3.1-His-C-MS-KIF18A resulted in expression of a 100 kDa His-tagged protein (FIG. 5B). The protein was immunoprecipitated by anti-His-tag antibody and immunoblotted with anti-MS-KIF18A. The obtained results are consistent with the bioinformatics predictions and the endogenous expression of MS-KIF18A.

Figure 6:
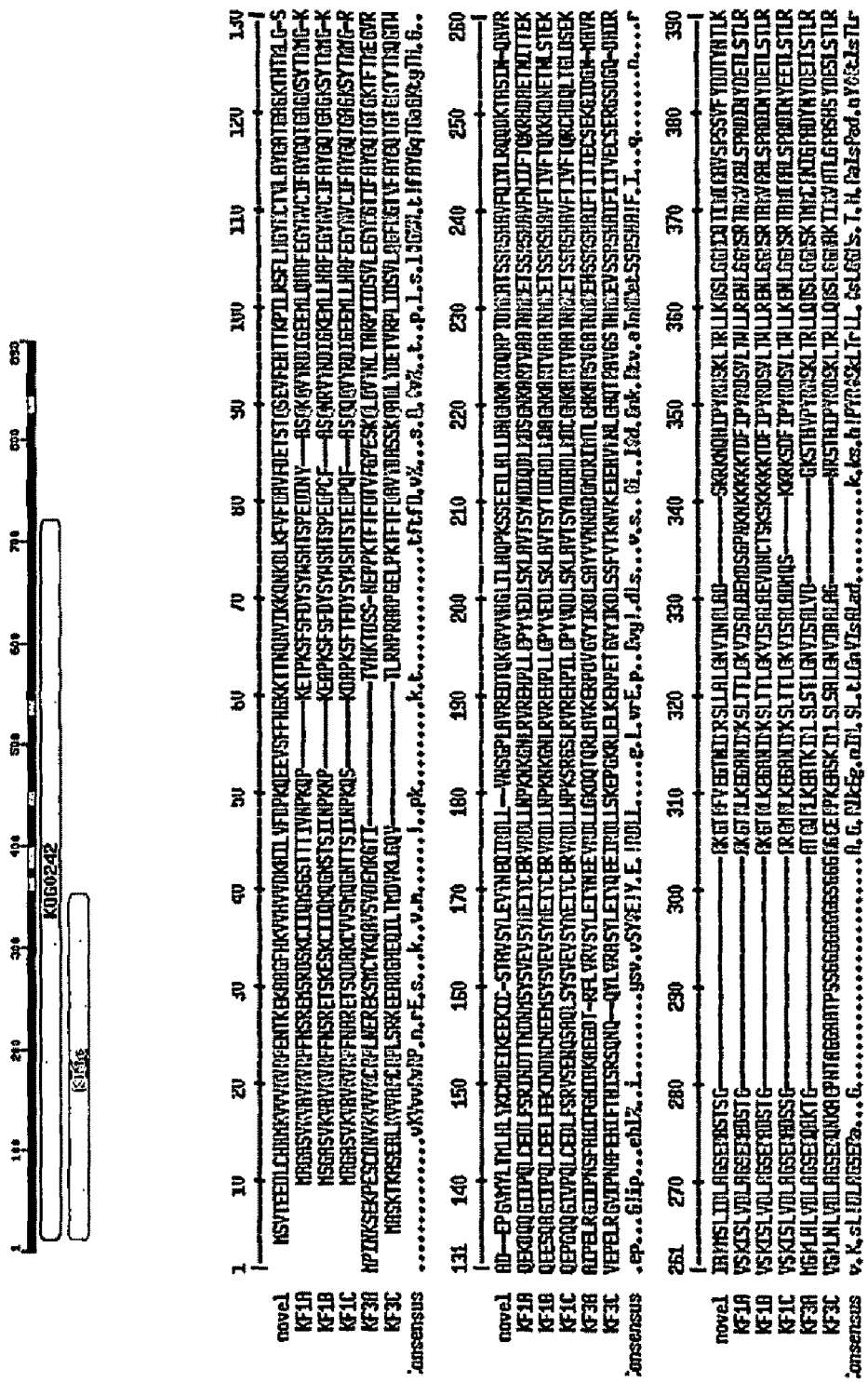
FIGS. 6A-B are schematic illustrations of the protein structure of MS-KIF18A.
Figure 7:
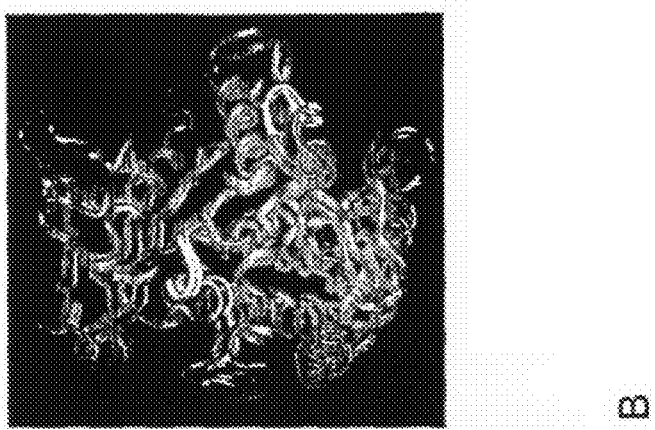
FIGS. 7A-B illustrate analyses of the MS-KIF18A motor domain.

Sequence analysis of the MS-KIF18A protein revealed that it belongs to the kinesin family of proteins. Kinesins are microtubule-associated motor proteins, which are responsible for movement on microtubules by use of ATP energy. Kinesins consist of a conserved motor domain, and a divergent coiled coil and cargo-binding domain. The MS-KIF18A motor domain is located between residues 9-363 and contains conserved ATP and microtubule-binding sites. Multiple sequence alignments of the MS-KIF18A motor domain with other kinesins demonstrated a high conservation of this region (FIG. 6B): A 60% homology was observed between the MS-KIF18A motor domain and other kinesins. An identity of 42% was observed between MS-KIF18A and conventional kinesin motor domains (FIG. 6B). The motor domain structure of conventional kinesin (kinesin 1) was resolved by X-ray crystallography which exists at the PDB database (pdbIBG2). Using a homology modeling approach analyzed by the Insight II program, the 3-D structure of MS-KIF18A motor domain could be predicted (using conventional kinesin as a template). The predicted tertiary structure of the MS-KIF18A motor domain (FIG. 7A) shows the same conformation as the template, suggesting a presence of functional microtubule and ATP-binding sites (FIG. 7B).

Figure 8:
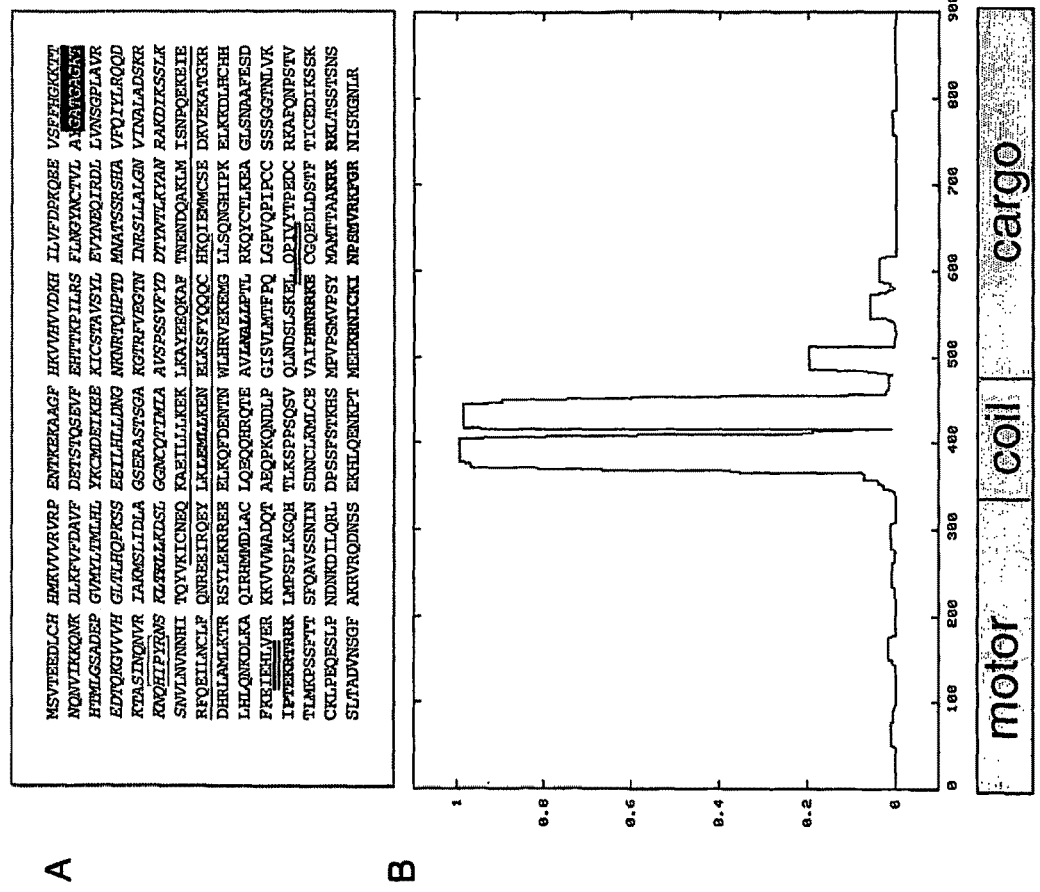
FIGS. 8A-B illustrate analyses of the MS-KIF18A polypeptide for known domains and motifs.

Secondary structure analysis revealed that the central region 375-453 AA of KIF18A is alpha-helical coiled-coil, followed by a unique cargo-binding domain at the C-terminus (FIG. 8). Conformational structures for the coiled-coil and cargo domains of non-conventional kinesins as well as the MS-KIF18A are not available to predict their 3-D structure.

Table 2 hereinbelow summarizes putative protein-protein interaction motifs in MS-KIF18A such as SH3, WW, AP-1 and FHA domains (ELM algorithm), that may regulate the MS-KIF18A partnership in various protein complexes.

TABLE 2

| Domain | Position |
|---|---|
| FHA domain interaction motif 1, threonine phosphorylation is required | Cargo-binding domain: 509-512, 719-722, 769-772, 824-827 |
| Class III PDZ domains binding motif | Motor domain: 5-8 Cargo-binding domain: 470-473, 499-502, 569-572, 604-607, 693-696, 763-766, 773-776, 786-789, 794-797 |

TABLE 2-continued

| Domain | Position |
|---|---|
| Class IV WW domains interaction motif; phosphorylation-dependent interaction. | Cargo-binding domain: 671-676, 681-686, 703-708 |
| Substrate motif for phosphorylation by CDK | Cargo-binding domain: 671-677 |
| CK1 phosphorylation site | Cargo-binding domain: 653-656, 684-687, 718-721, 726-729, 727-730, 768-771, 803-806, 804-807, 835-838, 838-841, 840-843 |
| CK2 phosphorylation site | Motor domain: 2-5<br>Cargo-binding domain: 492-495, 586-589, 771-774 |
| GSK3 phosphorylation recognition site | Cargo-binding domain: 727-731, 737-741, 806-810, 815-819, 834-838, 836-840, 837-841 |
| PKA phosphorylation site | Cargo-binding domain: 490-492, 567-569 |
| PKB Phosphorylation site | Cargo-binding domain: 829-835 |
| Motif recognized for modification by SUMO-1 | Motor domain: 147-150<br>Cargo-binding domain: 532-535, 624-627, 659-662, 682-685 |
| Nuclear localization signals | Cargo-binding domain: 662-668, 754-760, 828-831, 829-832, 874-890. |

MS-KIF18A protein is subjected to post-translational modification such as phosphorylation by CK1, PK1 and GSK3 (NetPhos algorithm). Sumolyation motifs were identified using SUMOplot and ELM algorithms at positions 147-151 (IKEE), 442 (LKLE), 532-535 (LKKD), 659-662 (VKIP) and 682-685 (LKSP). The SUMO-modifications regulate stability, activity (Gill, 2003, Curr. Opin. Genet. Dev. 13, 108-11; Seeler et al, 2003, Nat. Rev. Mol. Cell. Biol. 4, 690-699) and nuclear export of proteins (Wood et al., 2003, Proc. Natl. Acad. Sci. U.S.A. 100, 3257-62).

Nuclear localization signals (NLS) were identified at positions 662-668 (RKRK), 754-760 (PHNRRKE), 828-831 (KRKR), 829-832 (RKRK), and 874-890 (KRNICKINPSM VRKFGR) at the protein C-terminus.

Blast analysis for the homology of MS-KIF18A in mouse (NP_647464), rat (XP_342487), and zebra fish (NP_956533) resulted in an 84%, 81% and 63%, homology respectively which indicates conservation of KIF18A throughout evolution suggesting the importance of this protein.

MS-KIF18A sub-cellular distribution: The intracellular distribution of MS-KIF18A in MBA-15 cells was analyzed by indirect immunofluorescence microscopy (IF) using anti-MS-KIF18A. MS-KIF118A was observed at the nucleus, cytoplasm and plasma membrane ruffles (FIGS. 9A-I).

Nuclear localization of MS-KIF18A was observed with 30% of the cells having bright nuclear staining (FIG. 9A, arrows, 9B). Nuclear localization is regulated by nuclear localization signals (NLSs) identified at the protein C-terminus (Table 2). The protein was also detected in the cytoplasm (FIGS. 9D, G) and plasma membrane ruffles (FIG. 9B). IF demonstrated punctuate cytoplasmic staining of MS-KIF18A associated with microtubules (FIG. 9F, overlay) in MBA-15 cells. These results are in line with the conformational studies of the MS-KIF18A motor domain and suggest that MS-KIF18A has a microtubule binding site. Partial co-localization was observed between MS-KIF18A and cytoplasmic actin (FIGS. 9G-I).

Conclusion

This study identifies a new kinesin MS-KIF18A expressed by stromal cells. Structural properties of the MS-KIF18A protein were analyzed by bioinformatics, and were confirmed by biochemical studies and cell imaging.

Example 2

Intracellular Distribution of MS-KIF18A and EGFP-MS-KIF18A in Transiently Transfected MBA-15 Cells In order to further study the intracellular localization of MS-KIF18A, a construct comprising MS-KIF18A and green fluorescent protein was expressed in MBA-15 cells either alone or together with IL-2R.

Materials and Methods

Plasmids: pcDNA3.1-His-C-MS-KIF18A vector was generated as described in Example 1. EGFP-MS-KIF18A was generated by restricting pcDNA3.1-His-C-MS-KIF18A with KpnI and XbaI (New England Biolab, USA) and cloning the retrieved fragment into C-terminus of EGFP-C3 vector (Clontech, USA). pCMV-IL-2R was kindly provided by Dr. G. Hager, NCI, NIH, USA.

Transfection experiments: MBA-15 cells were grown on cover slips and transiently transfected with 1 µg of EGFP-MS-KIF18A DNA and 3 µg of pCMV-IL-2R DNA using Fugen6 reagent (Roche, USA). On the following day, cells were fixed and processed for immunofluorescent (IF) staining.

Confocal immunofluorescent microscopy: Transfected and non-transfected MBA-15 cells were fixed in 4% paraformaldehyde in phosphate buffered saline (PBS) for 20 minutes and permeabilized with 0.1% Triton in PBS for 5 minutes on ice. Cells were reacted with primary antibodies anti-MS-KIF18A (Luboshits and Benayahu, 2005, Gene 351: 19-28), anti-IL-2R (Upstate Biotechnologies, USA), anti-GM130 (Transduction Laboratories, USA), anti-KDEL receptor, anti-Lamin B (Santa Cruz, USA) or anti-caveolin-1 (Transduction Laboratories, USA) for 1 hour at room temperature (RT). Secondary antibodies conjugated to either fluorescein isothiocyanate (FITC), or Texas-Red (Jackson Immuno research Laboratories, USA) were reacted with the appropriate primary antibody for 1 hour at RT. Nuclei were stained with 4',6'-diamidino-2-phenylindole hydrochloride (DAPI, Molecular Probes USA). Slides were mounted using Prolong anti-fade mounting media (Molecular Probes, USA). Images were acquired on confocal microscope (Zeiss 510, Germany).

Transmission Electron Microscopy (TEM): Cells were fixed in 4% paraformaldehyde in PBS, pH, 7.4 for 1 hour at room temperature (RT) followed by treatment with 1% osmium tetra-oxide in PBS, pH, 7.4 for 2 hours, dehydration in ethanol and embedding in araldite. Ultra thin sections were cut with a diamond knife in LKB ultra microtome and sections were mounted onto formavar-coated grids. The grids were stained with uranyl acetate and lead citrate, and the sections were examined with a transmission electron microscope (Jeol, JEM 100CII).

Results

This study demonstrates the intracellular distribution of MS-KIF18A and EGFP-MS-KIF18A in transiently transfected MBA-15 cells. Confocal microscopy revealed the distribution of EGFP-MS-KIF18A in the cytosol and cell nucleolus (FIG. 10A). Anti-MS-KIF18A antibody staining was observed at the nucleus, dispersed throughout the cytoplasm, and localized at the plasma membrane ruffles (FIG. 10B), thereby demonstrating the same distribution as EGFP-MS-KIF18A (FIG. 10C). Lamin B is localized to the nuclear membrane in MBA-15 cells (FIG. 10D). LaminB does not show the same distribution as EGFP-MS-KIF18A (FIG. 10E-F). In addition, the localization of EGFP-MS-KIF18A was compared with ectopically expressed interleukin-2 receptor (IL-2R). The EGFP-MS-KIF18A that localizes to the plasma membrane (FIG. 10G) was partially co-localized with transfected IL-2R (FIGS. 10H-I) suggesting that MS-KIF18A is associated to plasma membrane structures.

The caveolae membrane system was analyzed in MBA-15 cells by transmission electron microscopy (TEM) and was observed as cell-surface invaginations (FIG. 11A; arrows). Further IF microscopy analysis for caveolin protein using anti-caveolin-1 identified its localization in patches scattered along the plasma membrane and at cytoplasmic areas (FIGS. 11C and 11F). Double staining with anti-MS-KIF18A and anti-caveolin-1 antibodies identified a partial co-distribution of these proteins in patches scattered along the plasma membrane (FIGS. 11D and 11G, arrows) and throughout the cytoplasm, indicating the MS-KIF18A is associated with the caveolae membrane system. The distribution of MS-KIF was compared with GM130 (a Golgi matrix protein, functioning in the late steps of ER-Golgi trafficking) and KDEL (an endoplasmic reticulum receptor). MS-KIF18A did not co-localize with either of these two proteins (FIGS. 12A-F).

Conclusion

MS-KIF18A localizes to various cellular structures, including the nucleus and the cytosol. MS-KIF18A localized at the plasma membrane, has been shown to co-localize with caveolin-1, the structural protein of the caveolae that decorates the membranes of cells and of caveosome bodies, "cavicles". Caveolae are lipid rafts known to participate in membrane signaling in a variety of cells, including osteoblasts (Solomon et al., 2000, J Bone Miner Res 15:2380-2390). Cavicles are transported from caveolae to the centrosomal region on microtubules; their trafficking suggested a role for kinesins in this movement (Pelkmans et al., 2001, Nat Cell Biol 3:473-483; Mundy et al., 2002, J Cell Sci 115:4327-4339). Caveolae were demonstrated by transmission electron microscopy and confocal imaging in MBA-15 cells. Anti-caveolin-1 staining showed a scattered pattern at cell membranes and at the peri-nuclear region, representing the caveosome. IF demonstrated an association between MS-KIF18A and caveolin-1 at the plasma membrane and in caveosomes.

MS-KIF18A also localizes at the nucleus. This localization relies on the NLS motifs identified in the cargo-binding domain and conserved sumoylation motifs. These motifs affect the dynamic of protein trafficking between nucleus and cytosol. The intracellular pattern of MS-KIF18A suggests that this protein can navigate between cellular compartments upon various modifications. MS-KIF18A is not associated with the nuclear membrane as no co-localization was observed with the nuclear lamina protein, Lamin B. Other kinesins, such as KIF5C and KIF5B, formed a complex with the nuclear pore protein, RanBP2 (Mavlyutov et al., 2002, Traffic 3:630-640).

Example 3

MS-KIF18A Protein Interacts with an Estrogen Receptor

The estrogen effect on cellular metabolism is mediated by two receptors (ERs), namely ERα and ERβ, both of which belong to the steroid nuclear receptor superfamily. The receptor consists of several domains: the A/B domain at the N-terminal encodes the ligand-independent activation function domain (AF1). AF-1 is responsible for protein-protein interactions and transcriptional activation of target genes. The DNA-binding domain (DBD) mediates the receptor binding to promoters of estrogen-regulated genes. Region D is a flexible hinge region between DNA and the ligand-binding domains (LBD). The C-terminal consists of the AF-2 domain, which is involved in interactions with transcriptional co-activators via nuclear receptor boxes, LXXLL-motifs. ERα and ERβ have been detected in various cells, including skeletal cells (e.g. osteoblasts, osteocytes and osteoclasts. ERα is expressed by two splice forms—the 66 kDa and the 46 kDa, which lacks the AF-1 domain. The estrogen receptor binds its ligand in the cytoplasm and is then translocated to the nucleus. The receptor may bind directly to a responsive gene via the estrogen response element (ERE) or, bind indirectly to a responsive gene by interacting with other transcription factors such as AP-1 and SP1. The nuclear signaling of estrogen occurs within 30-60 minutes following hormonal treatment. An alternative rapid (seconds to minutes) pathway is activation of Mitogen Activated Protein Kinases (MAPK) of proteins such as p38 and ERK1/2, an increase in ion concentration or Inositol 1,4,5-trisphosphate (IP3) which are mediators of non-genomic actions of estrogen.

Bioinformatic analysis of MS-KIF18A suggested a possible interaction between MS-KIF18A and the α estrogen receptor (ERα). Specifically, three nuclear receptor (NR) boxes, the LXXLL motifs, and two ΦXXΦΦ-like motifs at the coiled coil and cargo-binding domains of the protein were identified in MS-KIF18A. These motifs are known to mediate protein-protein interaction between transcriptional co-activators and between co-repressors and nuclear receptors. In addition, the cargo domain of MS-KIF18A contains a region homologous to the boundary region between the hinge and ligand-binding domains (LBD) of ERα (28.6% of identity) and at the coiled coil region of MS-KIF18A, a region homologous to the C-terminal of ERα-LBD (31% identity). Biochemical experiments were performed in order to verify the association of MS-KIF18A and ERα.

Materials and Methods

In vitro culture: Ex vivo primary cultured human mesenchymal stromal cells (MSC), MBA-15 and COS-7 cells were cultured as described in Example 1 hereinabove.

Estrogen signaling, ERK1/2 pathway: MBA-15 cells were maintained in medium supplemented with 3% charcoal striped FCS for 48 hours prior to the start of the experiment. On the day of the experiment, the cells were pretreated with 25 µM MAPK inhibitor, PD98059 (Calbiochem, USA) and an estrogen antagonist ICI 182,780 $10^{-6}$M (Tocris, USA) for 45 minutes. $10^{-8}$M 17β-estrogen (Sigma, USA) was added for five minutes. Cell lysates were used for immunoprecipitation and analyzed by Western blot.

Immunoprecipitation, Western blot, SDS-PADE gel: All experiments were performed as described in Example 1. Primary antibodies included anti-MS-KIF18A, anti-ER antibodies (Upstate Biotechnologies, USA) or SRA-1010 (Stressgen, Canada), anti-ERK1/2, pERK1/2 (Sigma, USA) or anti-His-tag (Santa Cruz Biotechnologies, USA). For detection a secondary antibody conjugated to biotin-extravidine-peroxidase and chemiluminescent substrate was used (Pierce, USA).

Plasmids: pcDNA3.1-His-C-MS-KIF18A vector was generated as described in Example 1. pSG5h-ERα66 was kindly provided by Dr. F. Gannon, EMBL, Heidelberg, Germany.

Transfection experiments: Expression constructs pcDNA3.1-His-C-MS-KIF18A and pSG5hER66 were transiently transfected into COS-7 cells using PolyFect reagent (Quiagen, USA). Cells were transfected with 1.5 µg of each vector in co-transfection experiments and 2.5 µg in single transfection experiments. After 16 hours, cells were harvested for immunoprecipitation and subsequent Western blot analysis.

Results

An anti-MS-KIF18A antibody was used to validate the association of the MS-KIF18A kinesin with ERα, both of which were ectopically expressed in COS-7 cells (FIGS. 14A-B) and between other endogenous proteins in MBA-15 cells (FIG. 15). COS-7 null cells were co-transfected with His-MS-KIF18A and ERα 66 kDa. Immunoprecipitation with anti-MS-KIF18A (FIGS. 14A and B, lane 5) or anti-His antibodies (FIGS. 14A and 14B, lane 4) followed by a Western blot with an anti-ERα antibody (FIG. 14A) demonstrated that ERα 66 kDa was pulled down by both anti-MS-KIF18A and anti-His antibodies. These results confirmed that there is an interaction between transfected His-MS-KIF18A and ERα 66 kDa.

The association of MS-KIF18A between endogenous proteins was analyzed in marrow stroma MBA-15 cells (FIG. 15). Proteins immunoprecipitated with anti-MS-KIF18A were analyzed by Western blot with two anti-ERα antibodies (SRA-1010 and AER311) which recognize different epitopes of the ERα. Immunoprecipitation analysis with a non relevant antibody (control) did not pull down the ERα (data not shown).

It is known that at least part of the non-genomic estrogen effect on cell metabolism is mediated via MAPK signaling pathways. MBA-15 cells were challenged with 17βE2 to measure its effect on activation of ERK1/2, a protein known to be involved in the MAPK signaling pathway. Western blot on whole cells lysates demonstrated an increase of pERK1/2 following 17βE2 stimulation. This increase was inhibited when the cells were pretreated with ICI 182,780 or PD98059 (FIG. 16A). This data demonstrates that estrogen triggers ERK1/2 in MBA-15 cells.

The association of MS-KIF18A with ERα (FIG. 16B) and pERK1/2 (FIG. 16D) was studied in response to stimulation with 17βE2. MBA-15 cells were treated with estrogen, ICI 182,780 or PD98059 under the same experimental procedure as described above. Following immunoprecipitation with anti-MS-KIF18A antibody, proteins were analyzed by Western blot (FIGS. 16B-D). An association between MS-KIF18A and ERα is shown in FIG. 16B. FIG. 16D demonstrates that pERK1/2 is also accounted in the MS-KIF18A-ERα complex. An increase in activated ERK was observed following estrogen treatment (FIG. 16D, lane 4), while pretreatment with PD98059 (FIG. 16D lane 2) or ICI 182,780 (FIG. 16D, lane 3) reduced ERK activation (FIG. 16E). Collectively, the data demonstrates that in MBA-15 cells, the estrogen response is associated with ERK1/2 activation and an association was demonstrated between MS-KIF18A and ERα.

Conclusion

The unique function of a motor protein is its interaction with a specific cargo. However, to date, only a few cargo molecules have been identified. To determine potential cargo for MS-KIF18A, bioinformatic techniques followed by biochemical experiments were employed. The bioinformatic predictions suggesting an interaction between MS-KIF18A and ERα. Such an association was confirmed using biochemical analyses on MBA-15 and COS-7 cell lysates. Co-immunoprecipitation of endogenous ERα in MBA-15 cells with MS-KIF18A by antibodies directed against MS-KIF18A confirmed the association between the two. Similarly, transfected ERα was co-immunoprecipitated with transfected MS-KIF18A in COS-7 null cells. In an earlier study, the association of ER with cytoskeleton proteins was suggested; however, no candidate has been proposed yet to underlie these observations (Zafar and Thampan, 1995, Biochem Mol Biol Int 36:1197-1206).

ERα is localized at the caveolar fraction of the plasma membrane (Chambliss and Shaul, 2002 Steroids 67:413-419; Kim et al., 1999, Biochem Biophys Res Commun 263:257-262). Caveolin-1 was shown to facilitate the translocation of ERα, and it was shown that endogenous caveolin-1 and ERα are associated both at the cytosol and plasma membrane (Razandi et al., 2003, Mol Cell Biol 23:1633-1646). Several members of the MAPK protein signaling pathway including ERK1/2 have been localized to caveolae (Yang et al., 2004, J Biol Chem 279:20898-20905; Li and Nord, 2004, Am J Physiol Renal Physiol 286:F711-719).

In summary, the data suggests an association between MS-KIF18A, ERα and caveolin-1. These interactions are presumably involved in the estrogen non-genomic response and the activation of the ERK pathway in MBA-15 cells.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

What is claimed is:

1. An isolated polynucleotide comprising a nucleic acid sequence as set forth in SEQ ID NO: 1 or SEQ ID NO: 3.

2. A method of identifying an agent that modulates estrogen signaling in a cell, comprising contacting the cell with an agent wherein a change in an expression and/or activity of a polypeptide comprising an amino acid sequence as set forth in SEQ ID NO: 2 in said cell is indicative that said agent is capable of modulating estrogen signaling in the cell.

3. The method of claim 2, wherein said agent is selected from the group consisting of an antibody, an antisense, an siRNA, a ribozyme and a DNAzyme.

4. The method of claim 2, wherein the cell is a mesenchymal stem cell or a testes cell.

* * * * *